(12) United States Patent
Lewis, Jr.

(10) Patent No.: US 9,492,687 B2
(45) Date of Patent: *Nov. 15, 2016

(54) LOW-PROFILE ULTRASOUND TRANSDUCER

(75) Inventor: George K. Lewis, Jr., Ithaca, NY (US)

(73) Assignee: ZetrOZ Systems, LLC, Trumbull, CT (US)

( * ) Notice: Subject to any disclaimer, the term of this patent is extended or adjusted under 35 U.S.C. 154(b) by 896 days.

This patent is subject to a terminal disclaimer.

(21) Appl. No.: 13/519,954

(22) PCT Filed: Jan. 3, 2011

(86) PCT No.: PCT/US2011/020062
§ 371 (c)(1),
(2), (4) Date: Jun. 29, 2012

(87) PCT Pub. No.: WO2011/082408
PCT Pub. Date: Jul. 7, 2011

(65) Prior Publication Data
US 2013/0006153 A1   Jan. 3, 2013

Related U.S. Application Data

(60) Provisional application No. 61/291,732, filed on Dec. 31, 2009, provisional application No. 61/291,779, (Continued)

(51) Int. Cl.
| | | |
|---|---|---|
| *A61N 7/00* | (2006.01) | |
| *A61B 8/00* | (2006.01) | |
| *A61B 17/225* | (2006.01) | |

(52) U.S. Cl.
CPC ............. *A61N 7/00* (2013.01); *A61B 8/4227* (2013.01); *A61B 8/4236* (2013.01);
(Continued)

(58) Field of Classification Search
USPC .................. 601/1–3; 600/407, 437, 446, 459
See application file for complete search history.

(56) References Cited

U.S. PATENT DOCUMENTS

| | | |
|---|---|---|
| 4,484,569 A | 11/1984 | Driller et al. |
| 4,784,148 A | 11/1988 | Dow et al. |
| (Continued) | | |

FOREIGN PATENT DOCUMENTS

| | | |
|---|---|---|
| EP | 0075273 A1 | 3/1983 |
| EP | 2091265 A1 | 8/2009 |
| (Continued) | | |

OTHER PUBLICATIONS

International Search Report and Written Opinion issued in PCT/US2011/020062, mailed Aug. 10, 2011.

*Primary Examiner* — Joel F Brutus
(74) *Attorney, Agent, or Firm* — FisherBroyles, LLP; Andrew K. Gonsalves, Esq.

(57) ABSTRACT

The present invention relates to a low-profile ultrasound transducer. The low-profile ultrasound transducer includes a piezoelectric component operative to receive a driving signal from an energy generating module and to emit the driving signal as ultrasonic energy. The piezoelectric component has a front surface and a back surface, and the energy generating module includes a plurality of electronic components. The low-profile ultrasound transducer also includes a lens component directly or indirectly deposited on the front surface of the piezoelectric component. The lens component includes a lens portion and a support portion. The lens portion of the lens component is configured to control the direction and wave pattern of the ultrasonic energy emitted from the piezoelectric component. The support portion of the lens component is configured to hold the piezoelectric component in place and to provide a chamber (Continued)

for housing at least one electronic component of the energy generating module. Methods of use and related devices are also disclosed.

28 Claims, 39 Drawing Sheets

Related U.S. Application Data filed on Dec. 31, 2009, provisional application No. 61/291,804, filed on Dec. 31, 2009.

(52) U.S. Cl.
CPC .......... *A61B 8/4281* (2013.01); *A61B 17/2251* (2013.01); *A61B 2017/2253* (2013.01); *A61N 2007/0078* (2013.01); *Y10T 29/49005* (2015.01)

(56) References Cited

U.S. PATENT DOCUMENTS

| | | | |
|---|---|---|---|
| 5,003,965 A | 4/1991 | Talish et al. | |
| 5,054,470 A | 10/1991 | Fry et al. | |
| 5,174,296 A | 12/1992 | Watanabe et al. | |
| 5,176,142 A | 1/1993 | Mason | |
| 5,211,160 A | 5/1993 | Talish et al. | |
| 5,467,779 A * | 11/1995 | Smith et al. | 600/445 |
| 5,492,126 A | 2/1996 | Hennige et al. | |
| 5,494,038 A | 2/1996 | Wang et al. | |
| 5,555,887 A | 9/1996 | Fraser et al. | |
| 5,577,507 A | 11/1996 | Snyder et al. | |
| 5,870,351 A | 2/1999 | Ladabaum et al. | |
| 5,882,300 A * | 3/1999 | Malinouskas et al. | 600/300 |
| 6,210,425 B1 | 4/2001 | Chen | |
| 6,217,530 B1 | 4/2001 | Martin et al. | |
| 6,251,073 B1 | 6/2001 | Imran et al. | |
| 6,322,527 B1 | 11/2001 | Talish | |
| 7,283,874 B2 | 10/2007 | Penner | |
| 7,311,679 B2 | 12/2007 | Desilets et al. | |
| 7,426,405 B2 | 9/2008 | Lee | |
| 2002/0135273 A1 | 9/2002 | Mauchamp et al. | |
| 2003/0018255 A1 | 1/2003 | Martin et al. | |
| 2003/0127947 A1 | 7/2003 | Chandran et al. | |
| 2003/0171700 A1* | 9/2003 | Martin et al. | 601/2 |
| 2005/0283110 A1 | 12/2005 | Atala et al. | |
| 2006/0184070 A1* | 8/2006 | Hansmann et al. | 601/2 |
| 2007/0016054 A1 | 1/2007 | Cao et al. | |
| 2007/0232962 A1 | 10/2007 | Zumeris et al. | |
| 2008/0033292 A1 | 2/2008 | Shafran | |
| 2008/0039746 A1* | 2/2008 | Hissong et al. | 601/3 |
| 2008/0045882 A1 | 2/2008 | Finsterwald | |
| 2008/0051680 A1 | 2/2008 | Luebcke | |
| 2009/0069486 A1 | 3/2009 | Yamashita et al. | |
| 2010/0152644 A1 | 6/2010 | Pesach et al. | |

FOREIGN PATENT DOCUMENTS

| | | | |
|---|---|---|---|
| EP | 2130495 A1 | | 12/2009 |
| KR | 2004/0022550 | | 3/2004 |
| WO | WO2007035529 | * | 3/2007 |

* cited by examiner

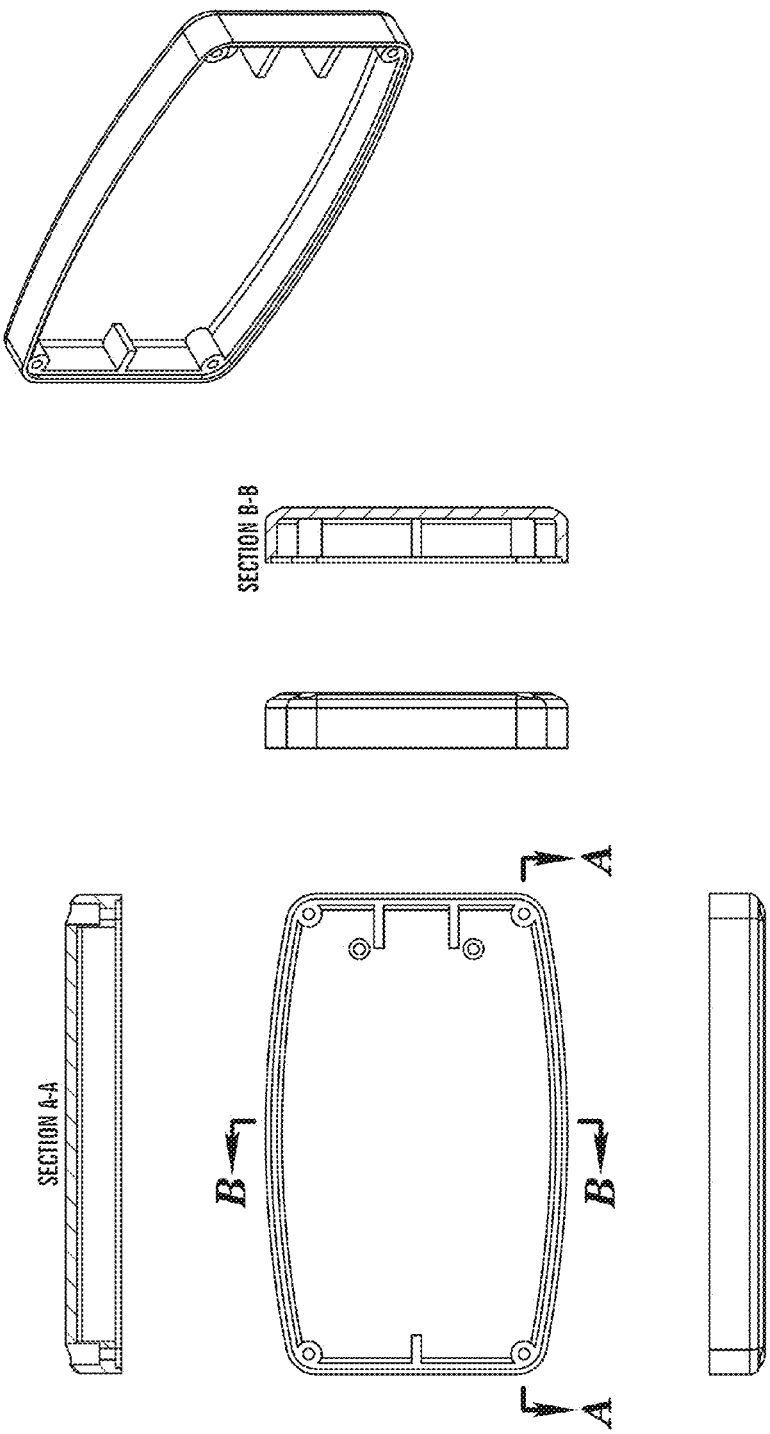

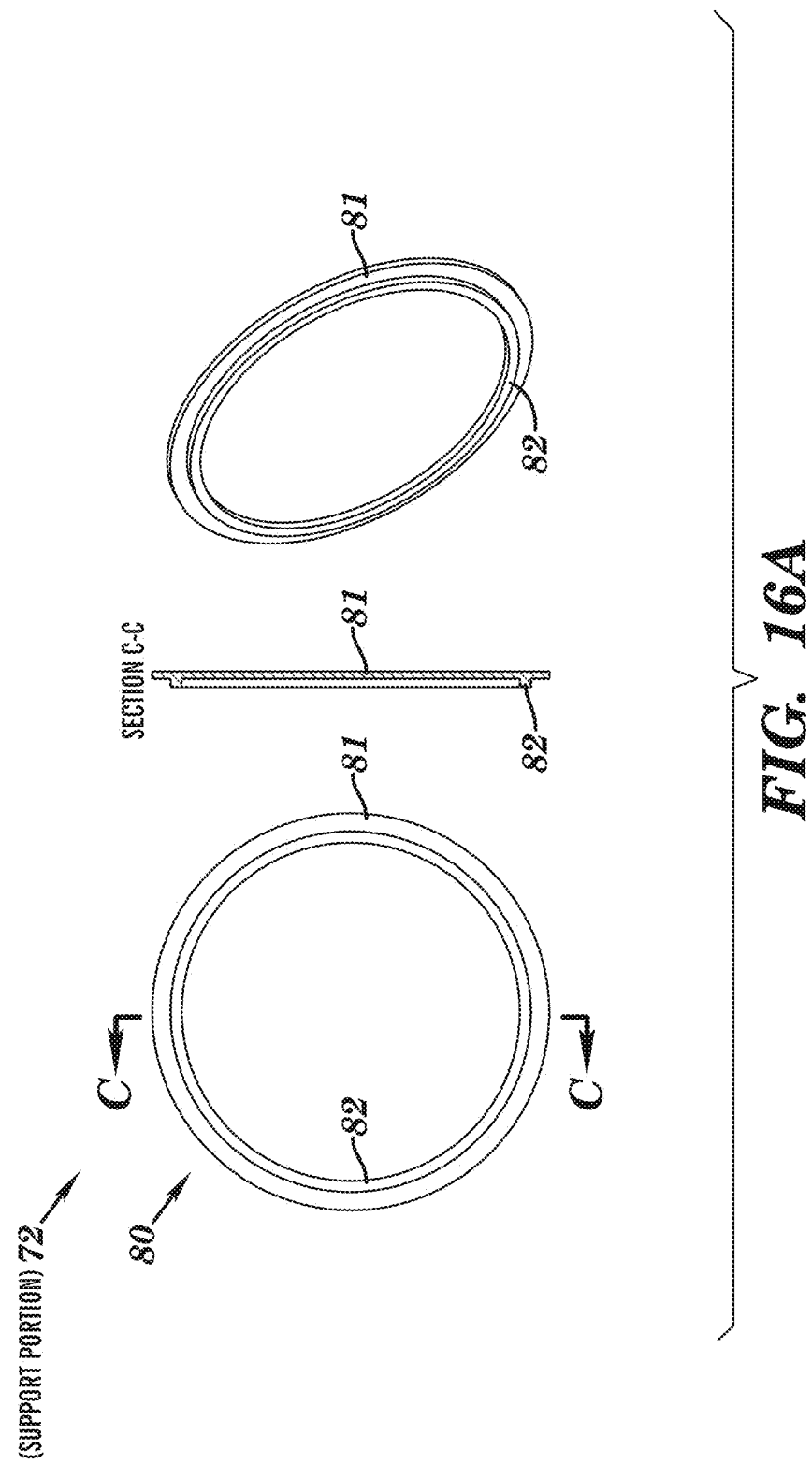

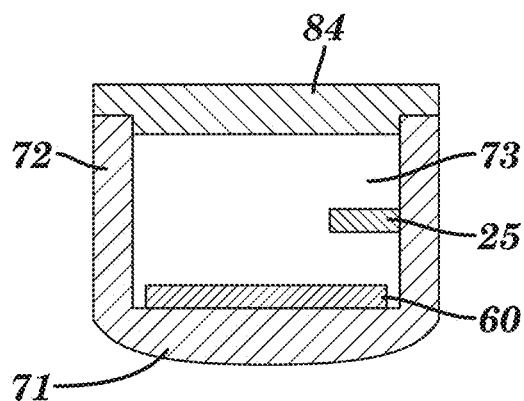
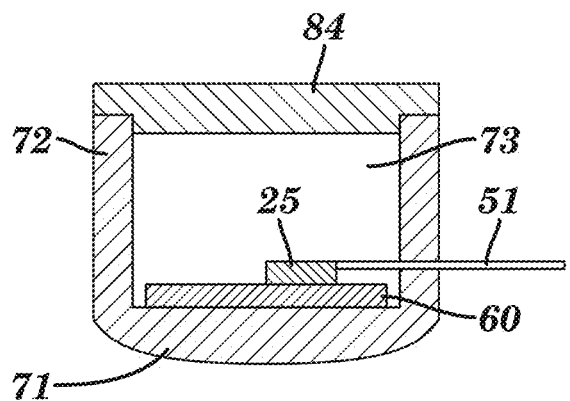
FIG. 22

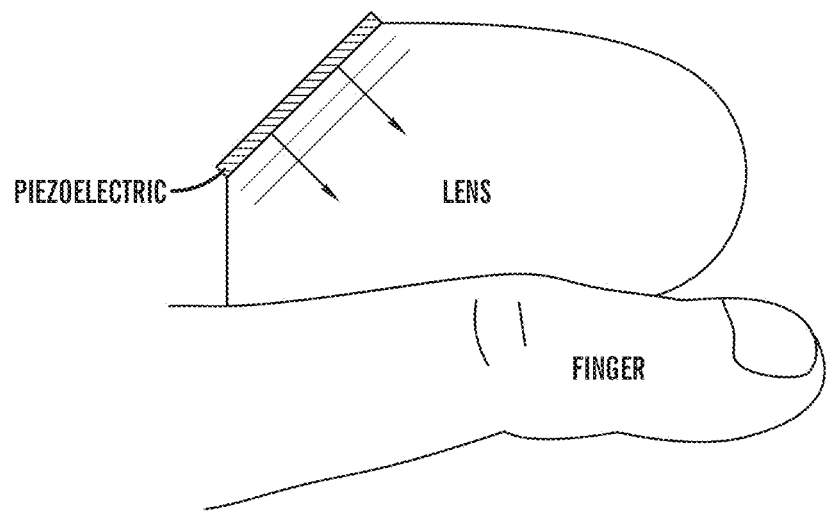
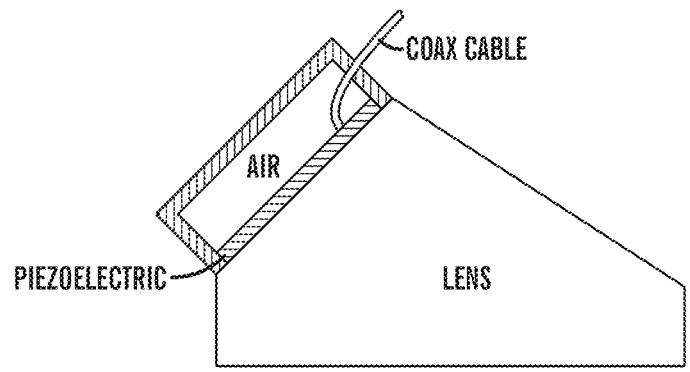
FIG. 28A

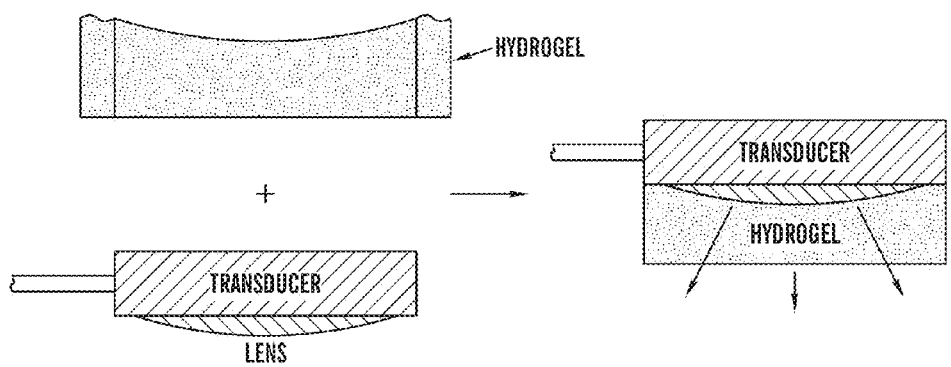
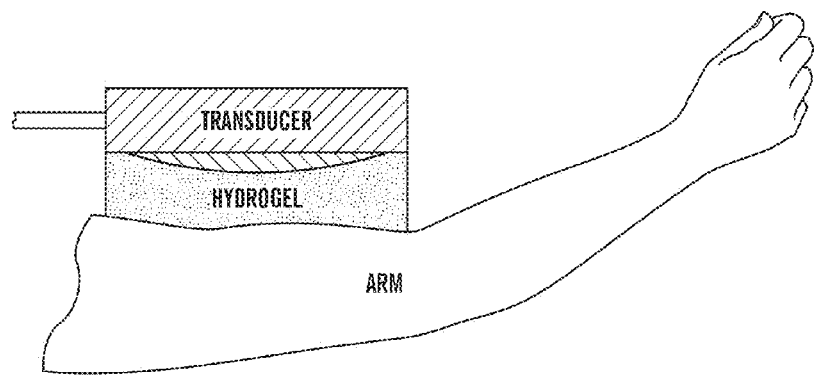
FIG. 28B

COIN ULTRASOUND DEVICE ARRAY
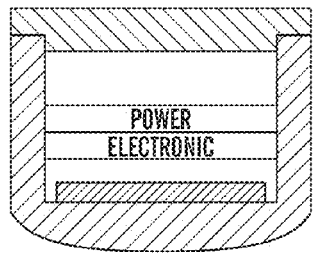
ONE COIN DEVICE CAN BE MADE INTO AN ARRAY
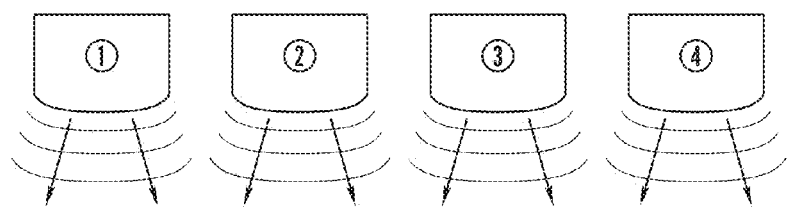
SIDE
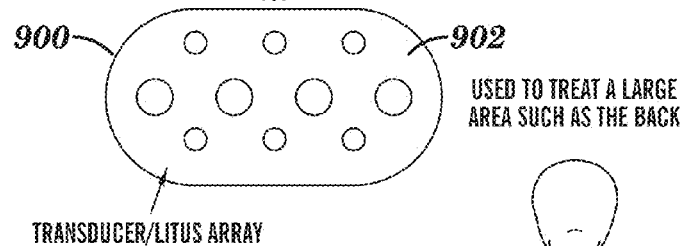
TOP
900 — 902
TRANSDUCER/LITUS ARRAY
USED TO TREAT A LARGE AREA SUCH AS THE BACK
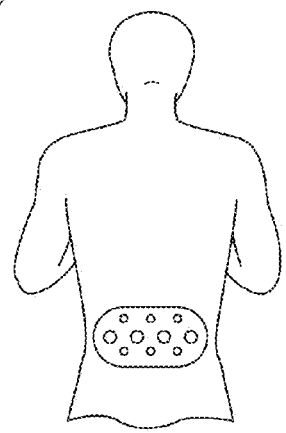
*FIG. 28C*

LOW-PROFILE ULTRASOUND TRANSDUCER

CROSS-REFERENCE TO RELATED APPLICATIONS

This application is a U.S. National Phase filing under 35 U.S.C. §371 of International Application No. PCT/US2011/020062, filed Jan. 3, 2011, and published as WO 2011/082408 on Jul. 7, 2011, which claims benefit of priority from U.S. Provisional Patent Application Ser. No. 61/291,732, filed Dec. 31, 2009, U.S. Provisional Patent Application Ser. No. 61/291,779, filed Dec. 31, 2009, and U.S. Provisional Patent Application Ser. No. 61/291,804, filed Dec. 31, 2009. The entire contents of each of the prior applications are incorporated herein reference in their entirety.

FIELD OF THE INVENTION

The present invention relates to a portable ultrasound system, devices containing the ultrasound system, and methods of using the ultrasound system. The present invention also relates to a low-profile ultrasound transducer, systems and devices containing the transducer, and methods of using the transducer.

BACKGROUND OF THE INVENTION

Traditional therapeutic ultrasound generation technologies have a number of deficiencies that prohibit their use in portable ultrasound delivery devices. For example, current therapeutic ultrasound generation technologies are, at the smallest, shoebox-sized devices that include a user interface, power generation circuitry, and a separate hand wand transducer attached via a cable. The devices vary in shape and size, but generally are 6-20 pounds. Such devices also require wall power and administer ultrasound energies from 0-4 Watts and at frequencies of from 1-3 MHz. The energy from the transducers of such devices is applied to penetrate into the tissue and administer ultrasound. Traditional ultrasound therapies are for a short duration (e.g., 5-20 minutes) where they are physically applied by hand for the entire treatment period. Other purported therapeutic ultrasound technologies purport to be portable, but are capable of producing only surface low-frequency 90 kHz ultrasound waves.

To date, there is a deficiency in the art for a portable (i.e., wearable) therapeutic ultrasound device that is able to safely deliver low to high frequency ultrasound (i.e., about 10 kHz to about 40 MHz) ultrasound energy deep into tissue. Further, therapeutic ultrasound devices in the art are not able to be used for long periods, due to safety concerns, the non-portable size of the devices or the need for external power sources or the need for the device to be actively applied by the user.

The present invention is directed to overcoming these and other deficiencies in the art.

SUMMARY OF THE INVENTION

In one aspect, the present invention relates to a portable ultrasound system that can be used for a wide range of ultrasound applications. The portable ultrasound system includes an energy generating module operative to generate a driving signal that can be transformed into ultrasonic energy, where the energy generating module includes a power source, an oscillator, and a driver component. The portable ultrasound system also includes an ultrasound transducer having a piezoelectric component and a lens component. The ultrasound transducer is operative to receive the driving signal from the energy generating module, to transform the driving signal into ultrasonic energy, and to control the direction of the ultrasonic energy emitted from the ultrasound transducer.

In another aspect, the present invention relates to an implantable device for use in generating ultrasound energy within a patient. The implantable device includes the portable ultrasound system of the present invention and an implantable component configured to contain the system.

In another aspect, the present invention relates to a biocompatible device for use in generating ultrasound energy within a patient. The biocompatible device includes an energy generating module operative to generate a driving signal that can be transformed into ultrasonic energy, where the energy generating module includes a power source, an oscillator, and a driver component. The biocompatible device also includes a piezoelectric component operative to receive the driving signal from the energy generating module, to transform the driving signal into low intensity therapeutic ultrasonic energy, and to emit the low intensity therapeutic ultrasonic energy. The biocompatible device also includes a biocompatible component configured to contain the energy generating module and the piezoelectric component.

In another aspect, the present invention relates to a low-profile ultrasound transducer. The low-profile ultrasound transducer includes a piezoelectric component operative to receive a driving signal from an energy generating module and to emit the driving signal as ultrasonic energy. The piezoelectric component has a front surface and a back surface, and the energy generating module includes a plurality of electronic components. The low-profile ultrasound transducer also includes a lens component directly or indirectly deposited on the front surface of the piezoelectric component. The lens component includes a lens portion and a support portion. The lens portion of the lens component is configured to control the direction and wave pattern of the ultrasonic energy emitted from the piezoelectric component. The support portion of the lens component is configured to hold the piezoelectric component in place and to provide a chamber for housing at least one electronic component of the energy generating module.

In another aspect, the present invention relates to a multi-unit transducer that includes a plurality of ultrasound transducers combined into a single multi-unit transducer, where at least one of the plurality of ultrasound transducers is a low-profile ultrasound transducer of the present invention.

In another aspect, the present invention relates to a method of making a low-profile ultrasound transducer. This method involves providing a piezoelectric component operative to receive a driving signal from an energy generating module and to emit the driving signal as ultrasonic energy, the piezoelectric component having a front surface and a back surface, and the energy generating module including a plurality of electronic components. The method also involves providing a lens component that includes a lens portion and a support portion. The method also involves directly or indirectly depositing the lens component on the front surface of the piezoelectric component, where the lens portion of the lens component is configured to control the direction and wave pattern of the ultrasonic energy emitted from the piezoelectric component, and where the support portion of the lens component is configured to hold the piezoelectric component in place and to provide a chamber for housing at least one electronic component of the energy generating module.

The present invention's portable ultrasound system and low-profile ultrasound transducer used in an ultrasound system can be used for various applications, some of which are briefly described as follows:

In one aspect, the present invention relates to a method for performing physiotherapy on a subject. This method involves providing a portable ultrasound system of the present invention or a plurality of the systems in the form of an array, and then applying therapeutic ultrasound energy to a target area of a subject, where the therapeutic ultrasound energy is generated by the system or array of systems.

In another aspect, the present invention relates to a method for applying ultrasound energy to a subject. This method involves providing a portable ultrasound system of the present invention or a plurality of the systems in the form of an array, and applying ultrasound energy to a target surface of a subject, where the ultrasound energy is generated by the system or array of systems.

In another aspect, the present invention relates to a method of topically delivering a drug to a subject. This method involves providing a portable ultrasound system of the present invention or a plurality of the systems in the form of an array, where the deliverable component includes a drug to be delivered to a subject, and applying ultrasound energy to a surface of a subject along with the deliverable component, where the ultrasound energy is generated by the system or array of systems.

In another aspect, the present invention relates to a method of internally delivering a drug to a subject. This method involves administering to a subject a biocompatible device of the present invention, where the biocompatible component is in the form of an ingestible device that includes a drug to be delivered to the subject, and where the device is effective to generate ultrasound energy in order to facilitate internal delivery of the drug to the subject.

As noted, for each of the above described methods, the low-profile ultrasound transducer of the present invention can be used as the transducer in the system.

Animal and clinical research has shown that therapeutic ultrasound is an effective method of increasing flexibility, decreasing recovery time, and improving the overall quality of life. The present invention is effective in providing a therapeutic ultrasound technology that packages ultrasound therapy options into a device that can be used all day long, with little to no discomfort, and little or no reduction of mobility. The device enables the application of ultrasound in a range of medical and non-medical applications in a small compact platform. Thus, the present invention provides, inter alia, a wearable therapeutic ultrasound system that is convenient and that can be used continuously for hours at a time.

The present invention further provides an ultra-portable, complete therapeutic ultrasound device that can be configured to include a power-source, ultrasound driver, and ultrasound transducer, and that can be controlled by the user in a single working unit. The device of the present invention produces ultrasound energies covering the therapeutic physiotherapy and drug delivery power ranges and frequencies, while still being much smaller in size and untethered by wires for eternal power as compared to current therapeutic ultrasound technologies. The complete therapeutic ultrasound device of the present invention is small enough to be placed inside a patch and can be used to apply ultrasound energy any place on the body for ultrasound administration.

The present invention therefore provides a wearable therapeutic ultrasound device that has the ability to provide ultrasound energy for extended periods of time during normal everyday activity. It therefore enables the safe use of ultrasound for healing, pain, drug delivery, and other applications over long periods of time. Further, this ultrasound system or device can be used for wireless energy transfer and recharging of implantable.

The invention could also be used for disposable ultrasound energy sources for military applications of sonar, mine detection, etc. For example, the present invention can be used for miniature and portable sources of ultrasound generation, i.e., for military, medical, and industrial applications. Further, the present invention can be used for sonar and as a low-cost portable diagnostic tool. The invention may also be used for tissue healing, wound healing, pain relief, and the like.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 12A is an illustration and FIG. 12B is a photograph of the portable ultrasound system.

FIGS. 13A-13B are illustrations of various aspects of one embodiment of housing 40 for use in the portable ultrasound system of the present invention. Although dimensions for the housing are shown, these are for illustrative purposes only and are not meant to limit all housings of the present invention to these dimensions.

FIG. 14A shows the transducer's lens component and piezoelectric component prior to assembly, and also generally depicts the size thereof in comparison to a United States quarter dollar coin. FIG. 14B shows the transducer with the lens component and piezoelectric component assembled to form the transducer.

FIG. 15A shows the lens component having lens portion 71 and support portion 72 combined as a single unit. FIG. 15B shows an unassembled low-profile ultrasound transducer having a lens component, a piezoelectric, and an electronic component 26 (e.g., a temperature sensor), where the electronic component 26 (e.g., temperature sensor) can be deposited directly onto the back surface of the piezoelectric component, though it need not be deposited directly thereto.

FIGS. 16A-16B are illustrations of one embodiment of a support portion 72 of a low-profile ultrasound transducer of the present invention. The support portion 72 is configured as a ring 80 having an outer ring portion 81 and an inner ring portion 82. FIG. 16A provide perspective views of support portion 72. Although dimensions for the support portion are shown, these are for illustrative purposes only and are not meant to limit all such support portions of the present invention to these dimensions. FIG. 16B shows a ring support portion 72 combined with piezoelectric component 60 and lens portion 71.

FIG. 22 shows cross-sectional views of various embodiments of a low-profile ultrasound transducer of the present invention. The transducers shown are configured to include a temperature sensor 25 directly on or near the back surface of the piezoelectric component 60 within chamber 73.

FIGS. 28A-28C are illustrations showing various uses of embodiments of the low-profile ultrasound transducer of the present invention.

FIG. 30A: Power vs. time. FIG. 30B: Intensity vs. time. FIG. 30C: Intensity vs. penetration depth.

DETAILED DESCRIPTION OF THE INVENTION

The present invention relates to a portable ultrasound system as well as a low-profile ultrasound transducer that are suitable for a number of ultrasound applications, including, for example, therapeutic ultrasound, wireless energy transfer and charging on internal devices, brain drug delivery, thermal drug delivery, cosmetic applications, bone healing, and others. The portable ultrasound system and low-profile ultrasound transducer are particularly suited for tissue stimulation, ultrasound therapy, healing, regenerative medicine, drug delivery, ocular drug delivery, and as portable sources of ultrasound.

The portable ultrasound system of the present invention is operative to emit ultrasonic energy as pulsed, continuous, or both pulsed and continuous ultrasonic energy. The portable ultrasound system is operative to ultrasonic energy having an acoustic intensity ranging from between about 10 mW/cm$^2$ and about 5 W/cm$^2$. Further, the portable ultrasound system of the present invention requires relatively low power and voltage to produce ultrasound in this acoustic intensity range. This enables the portable ultrasound system to be used in wide range of ultrasound applications, particularly those applications that require portability and that do not require trained medical or therapeutic personnel.

The portable ultrasound system of the present invention and the low-profile ultrasound transducer of the present invention are well suited for use together, with the low-profile ultrasound transducer being used in the portable ultrasound system. However, other transducers may also be used in the portable ultrasound system of the present invention. As set forth herein, the portable ultrasound system is disclosed, followed by the low-profile ultrasound transducer.

Portable Ultrasound System

Figure 1:
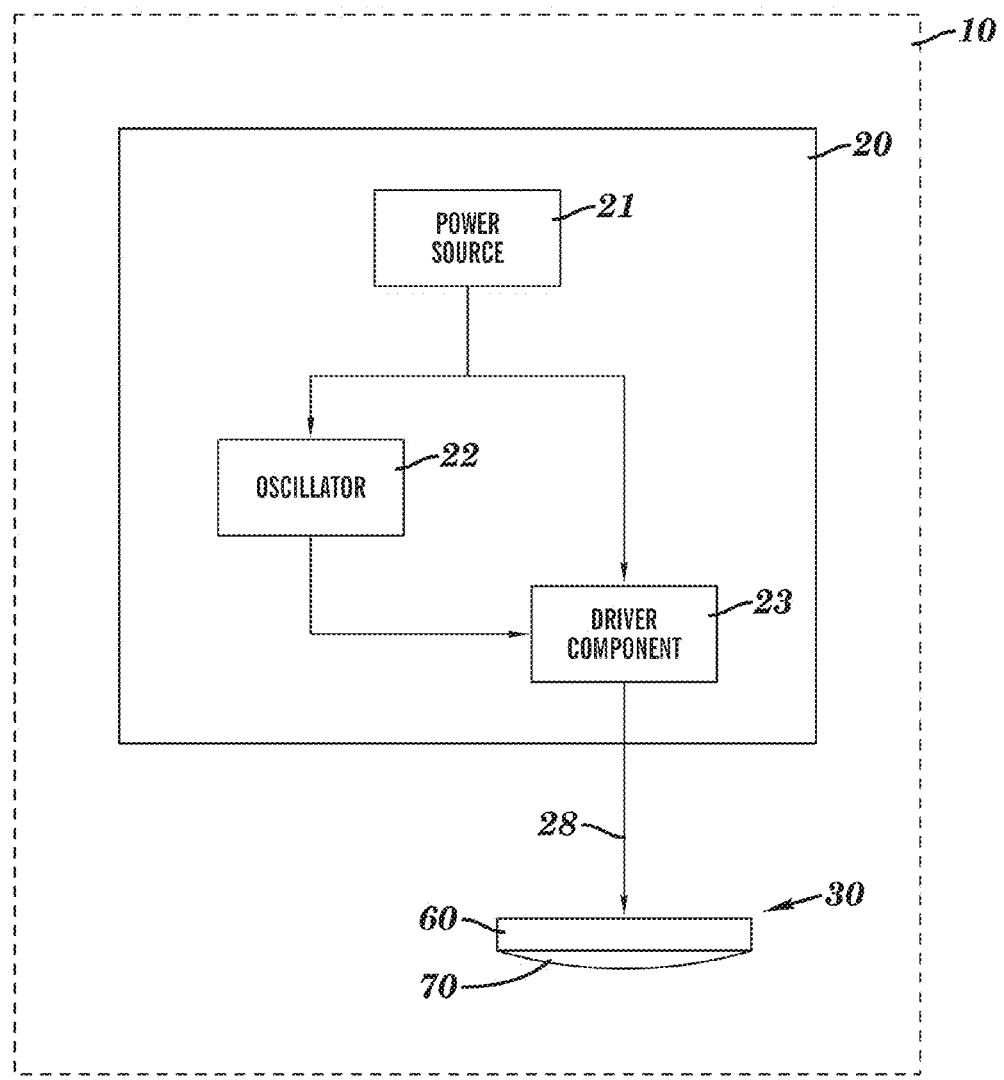
FIG. 1 is a schematic drawing of one embodiment of the portable ultrasound system of the present invention.

FIG. 1 is a schematic drawing of the portable ultrasound system of the present invention. As shown in FIG. 1, portable ultrasound system 10 includes energy generating module 20 and ultrasound transducer 30. Energy generating module 20 includes power source 21, oscillator 22, and driver component 23, so that energy generating module 20 is operative to generate a driving signal 28 that can be transformed into ultrasonic energy. Ultrasound transducer 30 includes piezoelectric component 60 and lens component 70. Ultrasound transducer 30 is operative to receive the driving signal 28 from energy generating module 20, to transform the driving signal into ultrasonic energy, and to control the direction of the ultrasonic energy emitted from ultrasound transducer 30.

Figure 2A:
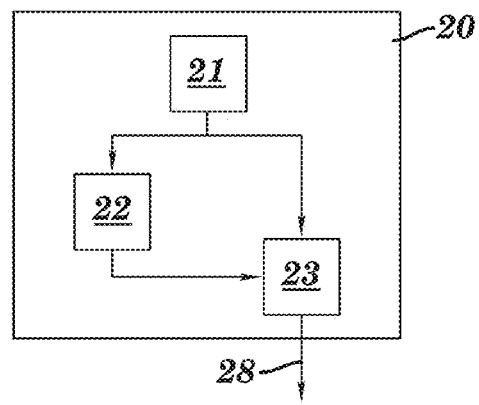
FIGS. 2A-2C are schematic drawings of various embodiments of the energy generating module 20 of the portable ultrasound system of the present invention.
Figure 2B:
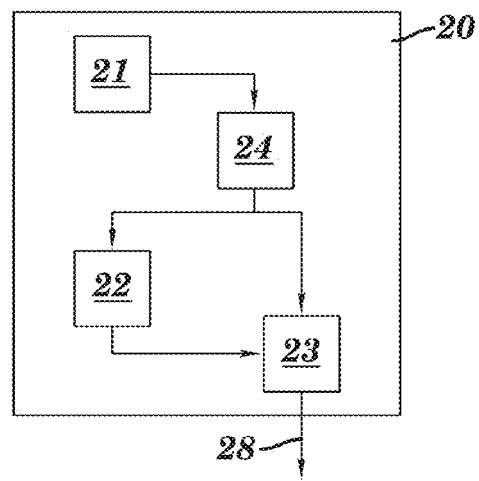
Figure 2C:
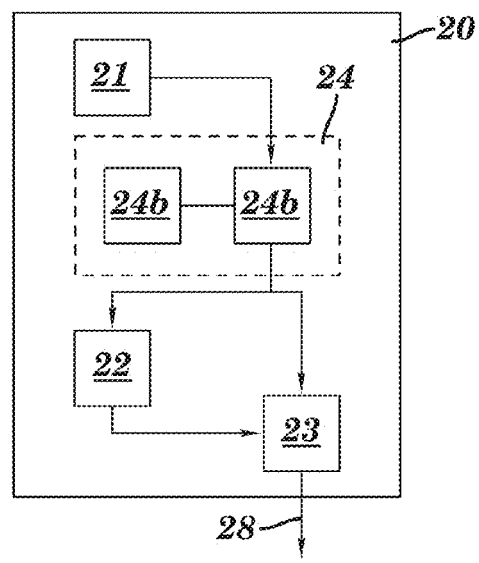

As shown in FIGS. 2A-2C, energy generating module 20 can be provided in various operative configurations. Each configuration is designed to provide a voltage efficiency of voltage load input (from power source 21) to voltage load output (exiting driver component 23) of at least 80 percent. The present invention includes all voltage efficiencies of at least 80 percent and above, including, for example, but not limited to, ranges from about 80 percent to more than 99 percent voltage efficiency.

As shown in FIG. 2A, in one embodiment, energy generating module 20 includes power source 21 coupled to both oscillator 22 and driver component 23, so that power source 21 provides power to both oscillator 22 and driver component 23.

As shown in FIG. 2B, in one embodiment, energy generating module 20 can further include voltage controller 24, which is operative to control power distribution (e.g., as an on/off power switch) from power source 21 to oscillator 22 and driver component 23. In a particular embodiment, voltage controller 24 can include on/off controller 24a coupled to transistor switch 24b. A suitable on/off controller or supervisory IC 24a can include, without limitation, LTC29511TS8-2, TPS3707-30DGN, and the like. A suitable transistor switch 24b can include, without limitation, MOSFETs (e.g., FDY102PZ, EL7158S, Si9433BDY, and the like) configured to be used as power switches.

In one embodiment, oscillator 22 is configured to operate in a range of between about 0 MHz and about 40 MHz at voltages ranging from between about 0 and 5 volts. In one embodiment, the oscillator can be configured to operate from about 0-5 volts, while the driver can be configured to operate from about 0-24 volts to power the ultrasound transducer. In low intensity treatments, for example, the driver can be configured to operate at about 0-5 volts.

The portable ultrasound system of the present invention can run on power generated at between about 0.1 and about 24 volts. Thus, power source 21 can include any device operative to generate between about 0.1 and about 24 volts. For example, suitable power sources 21 can include, without limitation, various types of batteries, including non-rechargeable and rechargeable batteries. Examples of suitable batteries include, without limitation, double A batteries (AA), Lithium ion batteries, and the like. The portable ultrasound system of the present invention is configured so that it can run on a single, off-the-shelf battery for maximum portability, or configured to run on more than one battery where portability or size of the system is less important to the user.

Figure 3A:
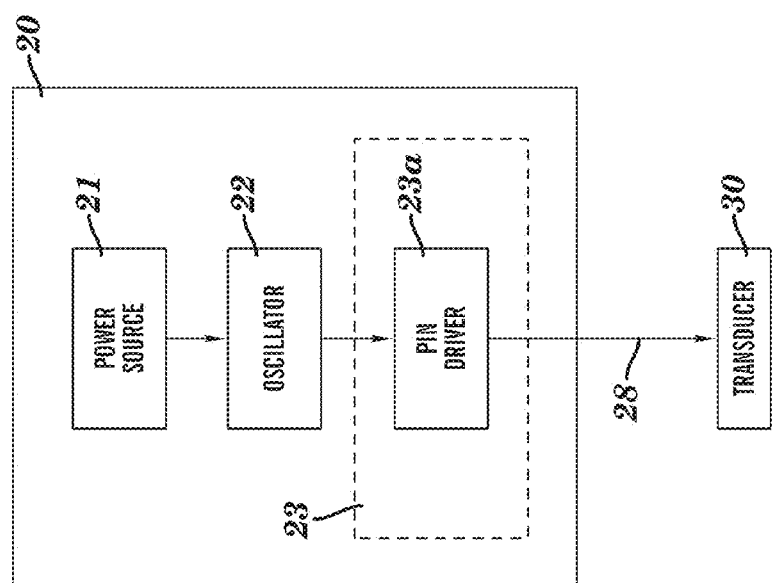
FIGS. 3A-3D are schematic drawings of various embodiments of the portable ultrasound system of the present invention.
Figure 3B:
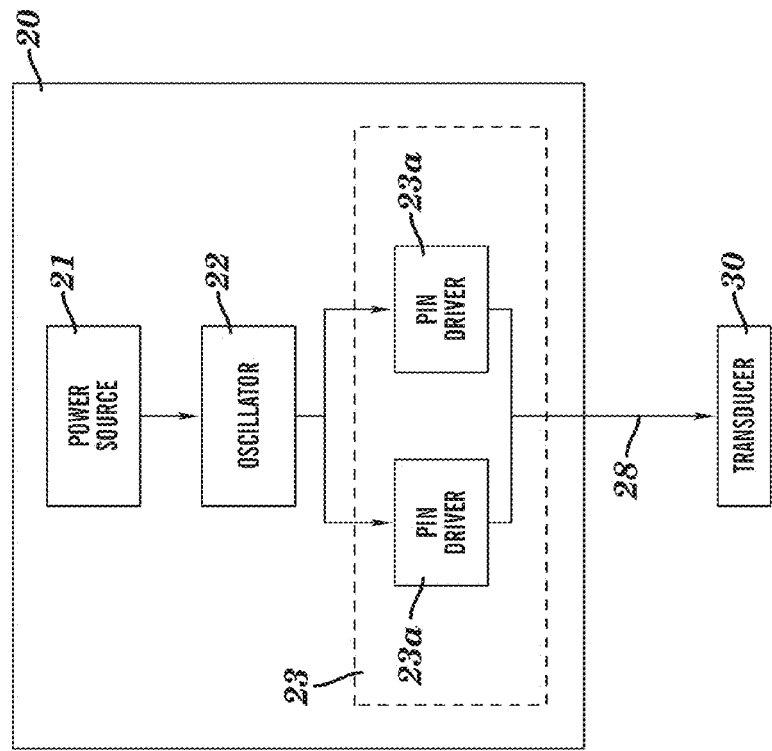
Figure 3C:
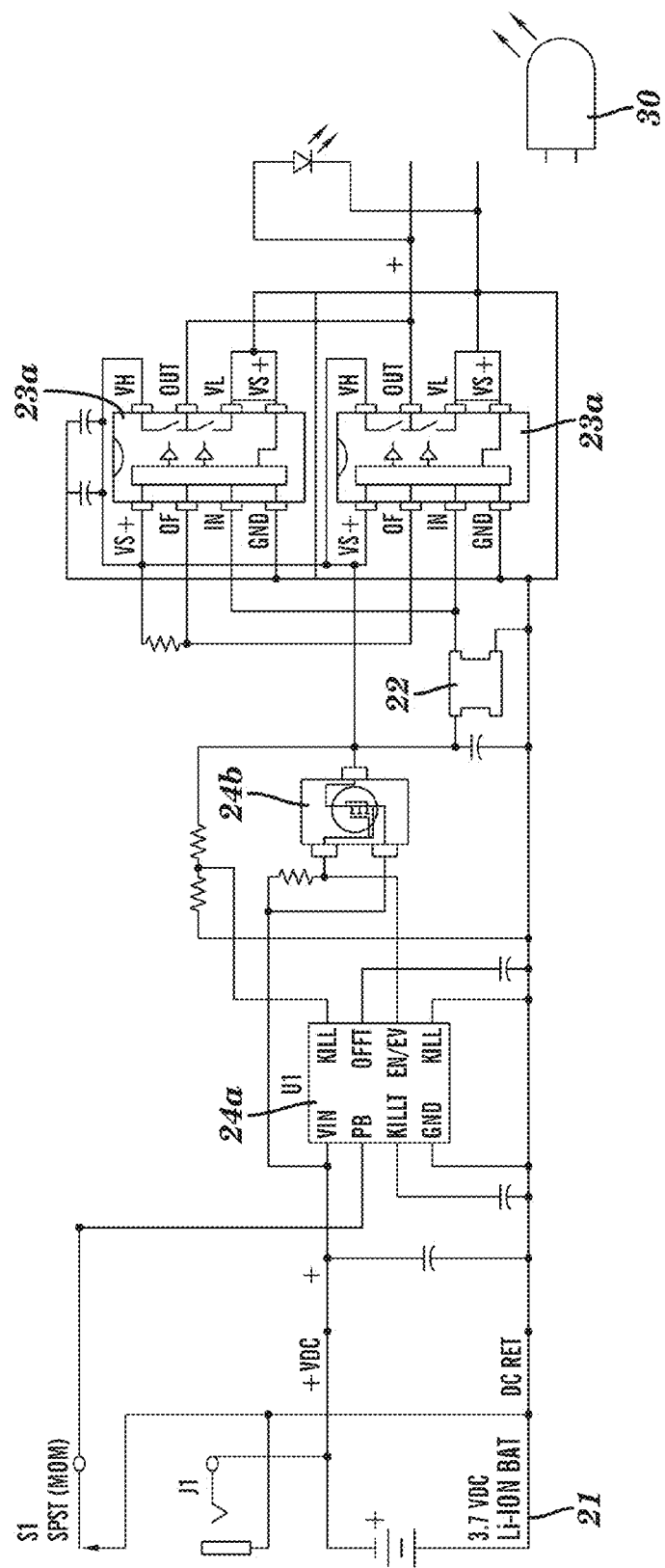
Figure 3D:
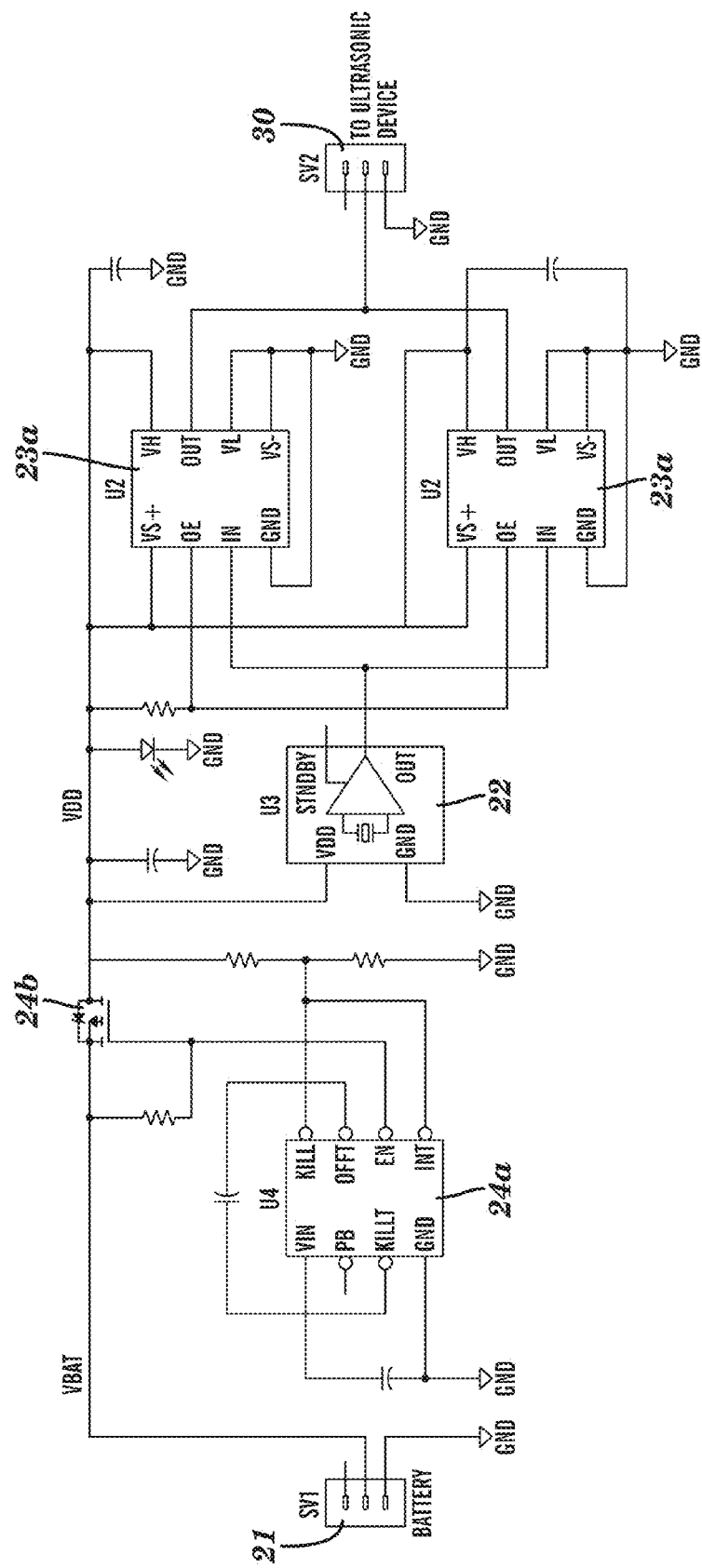

As shown in FIG. 3A, driver component 23 can include at least one pin driver 23a. As shown in FIGS. 3B-3D, in particular embodiments, driver component 23 can include two pin drivers 23a arranged in parallel. Further embodiments can include more than two pin drivers 23a, arranged in parallel, in series, or in both parallel and series. FIG. 3C and FIG. 3D illustrate detailed circuitry of particular embodiments of energy generating module 20. However, the present invention is not limited to circuitry configurations illustrated in FIGS. 3C-3D, which are being provided only as illustrative examples.

Figure 4:
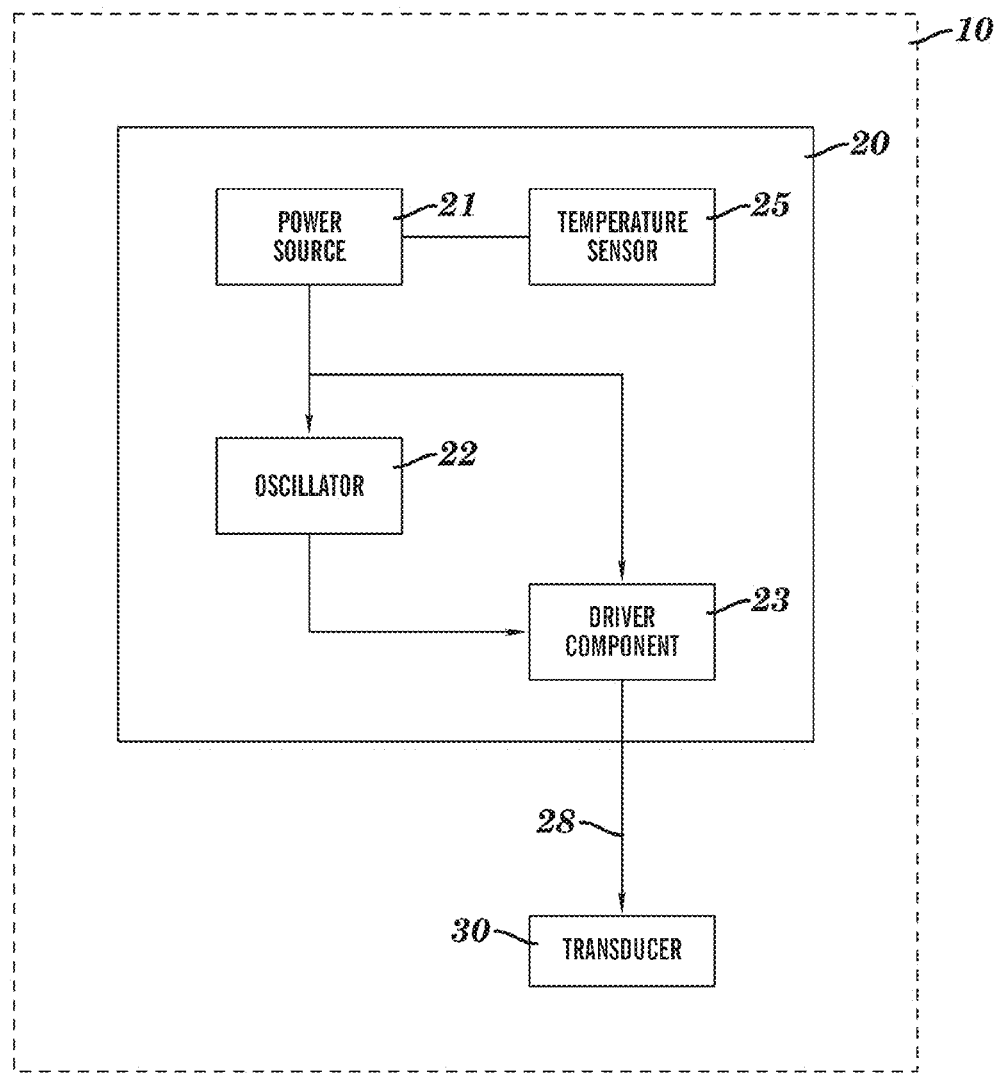
FIG. 4 is a schematic drawing of one embodiment of the portable ultrasound system of the present invention.

As shown in FIG. 4, a further embodiment can include temperature sensor 25 (e.g., SA56004BDP,118) as part of energy generating module 20. Suitable temperature sensors 25 can include any device operative to monitor heat generated during use of portable ultrasound system 10, and to turn off or cancel power generation from power source 21 when the temperature of portable ultrasound system 10 reaches a predetermined high temperature cut-off point. Thermal cut-offs that turn power off when the temperature rises beyond a set point. Suitable temperature sensors 25 are known in the art. As shown in FIG. 22, temperature sensor 25 can be deposited on or near piezoelectric component 60.

Figure 5A:
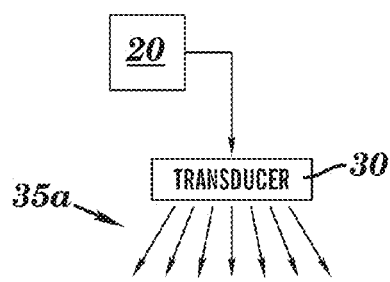
FIGS. 5A-5D are schematic drawings of various embodiments of the portable ultrasound system of the present invention. Various wave patterns produced by the transducer are shown.
Figure 5B:
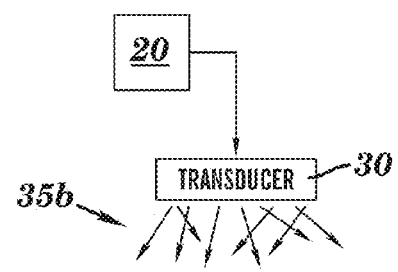
Figure 5C:
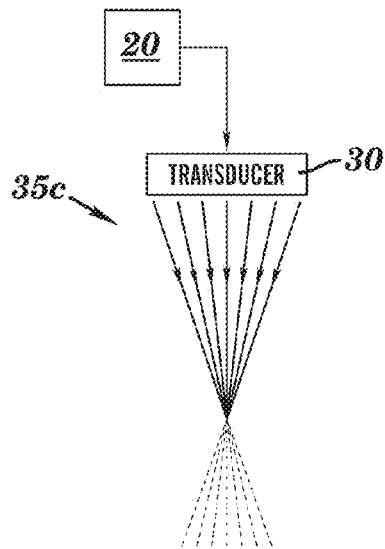
Figure 5D:
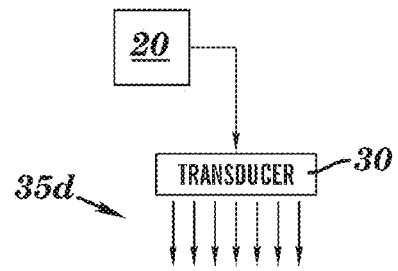

The portable ultrasound system of the present invention is useful for applying ultrasonic energy to a target area (e.g., of a human or animal subject) in a targeted and controlled manner. For example, as illustrated in FIGS. 5A-5D, the portable ultrasound system is effective in controlling the direction and wave pattern of the ultrasonic energy emitted from the portable ultrasound system. As shown in FIGS. 5A-5D, ultrasound transducer 30 can be configured to control the direction of emitted ultrasonic energy 35 in various wave patterns, including diverging wave pattern 35a (FIG. 5A), scattering wave pattern 35b (FIG. 5B), focused wave pattern 35c (FIG. 5C), and parallel wave pattern 35d (FIG. 5D).

Figure 6A:
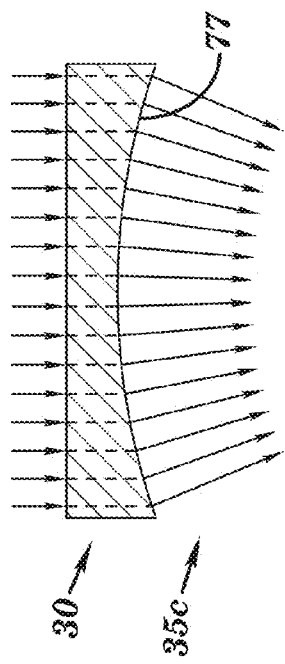
FIGS. 6A-6D are schematic drawings of various embodiments of the ultrasound transducer of the present invention. Various wave patterns produced by the transducer are shown.
Figure 6C:
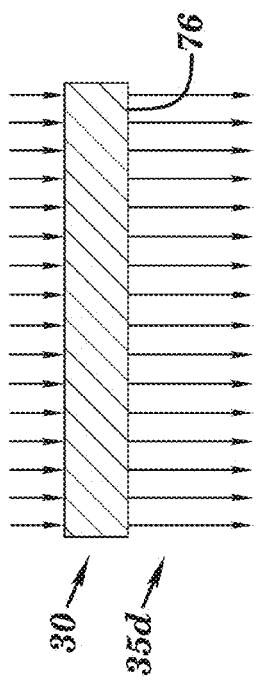
Figure 6B:
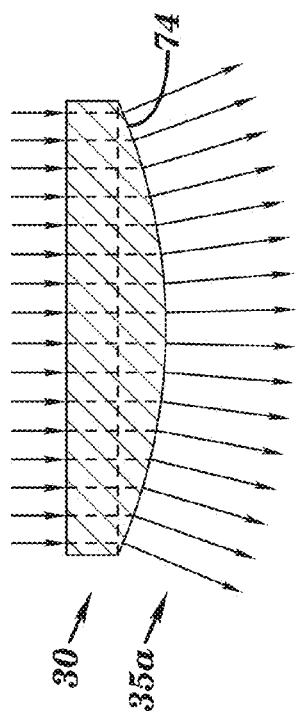
Figure 6D:
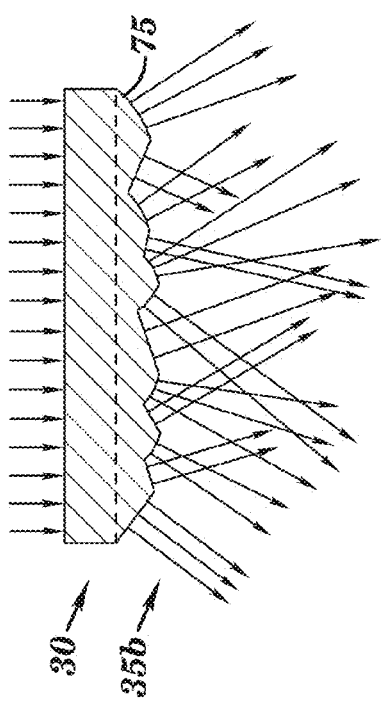

As shown in FIGS. 6A-6D, to control the direction and type of wave pattern of the emitted ultrasonic energy, lens component 70 of ultrasound transducer 30 can be configured to include an outer lens surface that as follows: convex lens 74 for diverging wave patterns 35a (FIG. 6A), ridged lens 75 for scattering wave patterns 35b (FIG. 6B), concave lens 77 for focused wave patterns 35c (FIG. 6C), or flat lens 76 for parallel wave patterns 35d (FIG. 6D). Also, the present invention can use a directed lens to take into account directing ultrasound waves into a subject's body at specific angles (e.g., toward a joint within the body).

Figure 7:
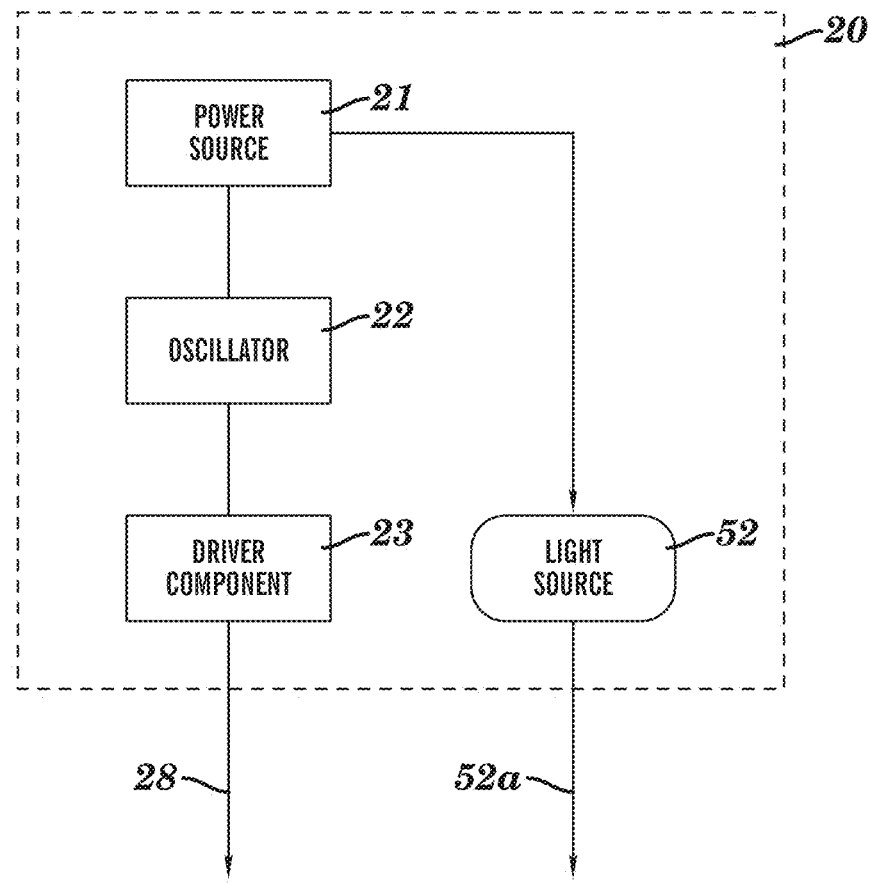
FIG. 7 is a schematic drawing of one embodiment of the energy generating module 20 of the portable ultrasound system of the present invention.

As shown in FIG. 7, energy generating module 20 can be configured to also include light source 52, which can be used to emit light energy 52a. Light source 52 is integrated into energy generating module 20 so that it is powered by power source 21. Light source 52 can include any device operative to convert electrical energy received from power source 21 into light energy 52a. In one embodiment, light source 52 can include a light-emitting diode (LED). The emitted light energy 52a can be useful for various purposes, including, without limitation, as heat therapy, light therapy, light signaling, lighting, and decorative purposes.

Figure 8A:
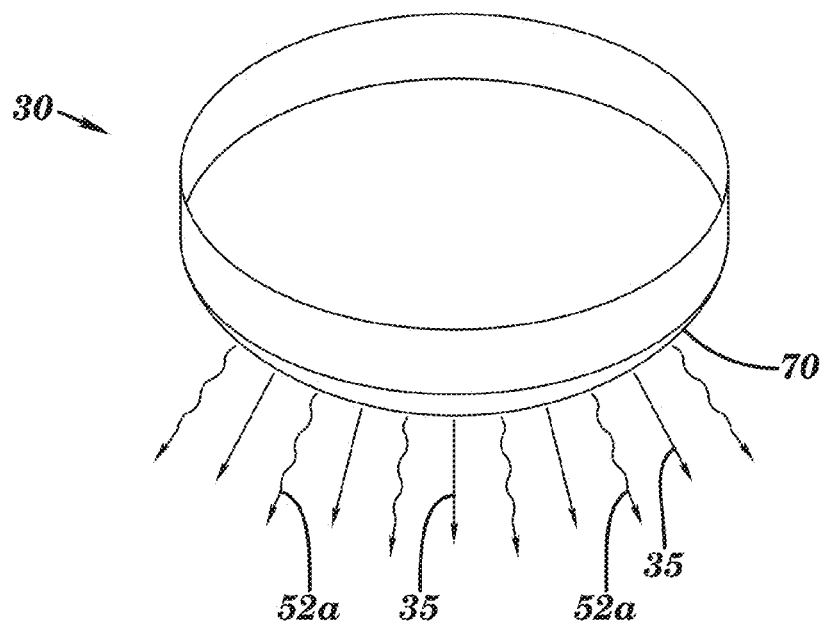
FIGS. 8A-8B are illustrations showing various embodiments of the ultrasound transducer of the present invention. As shown, these embodiments of the ultrasound transducer allow both ultrasonic energy (depicted as straight arrows) and light energy (depicted as wavy arrows) to pass therethrough.
Figure 8B:
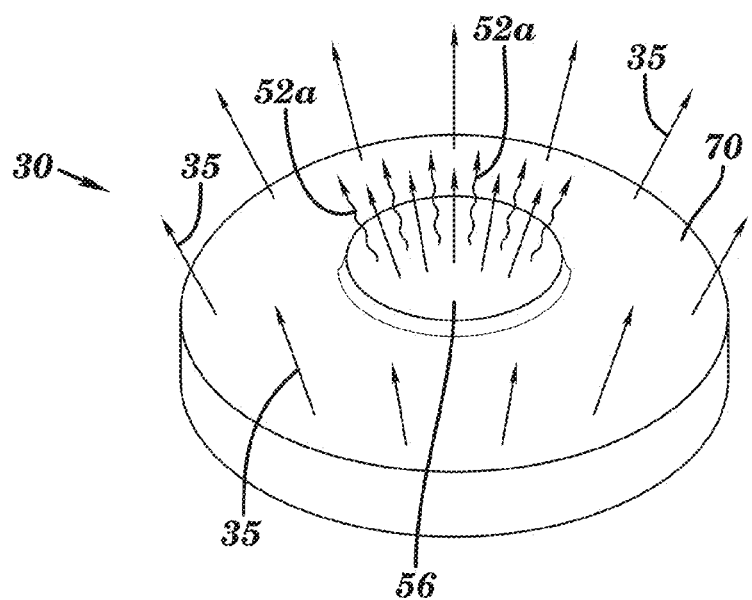

As shown in FIGS. 8A-8B, lens component 70 can be configured to operate to allow both ultrasonic energy 35 and light energy 52a to be emitted from ultrasound transducer 30 to pass through lens component 70. However, lens component 70 can also be configured to allow only ultrasonic energy 35 to pass through lens component 70. Various materials can be used for lens component 70, including, without limitation, the following materials: Ultem, Rexolite, Ahrilic, Plexiglass, and the like. Suitable materials for passing only ultrasonic energy 35 through lens component 70 are known in the art and contemplated by the present invention. Suitable materials for passing both ultrasonic energy 35 and light energy 52a through lens component 70 are also known in the art and contemplated by the present invention. Further, as shown in FIG. 8B, lens component 70 can be configured so that only a portion 56 of it is suitable for passing both ultrasonic energy 35 and light energy 52a therethrough, with the rest of lens component 70 configured to allow for passing of only ultrasonic energy 35 therethrough. As used in the drawings of the present invention, wavy arrowed lines generally depict light energy 52a and straight arrowed lines generally depict ultrasonic energy 35 or driving signal 28.

Figure 9:
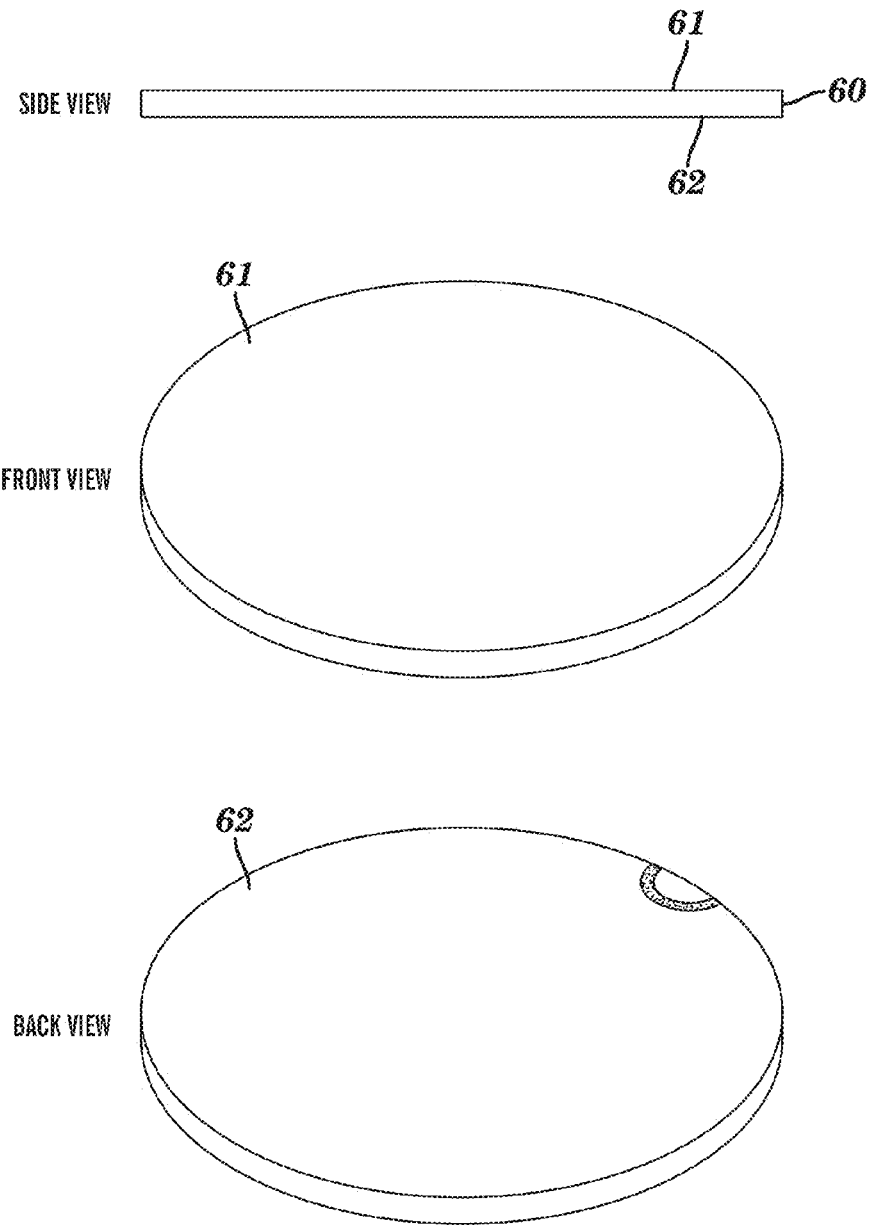
FIG. 9 are perspective views of one embodiment of a piezoelectric component for use in the present invention. Side view, front view, and back view perspectives are shown.
Figure 10A:
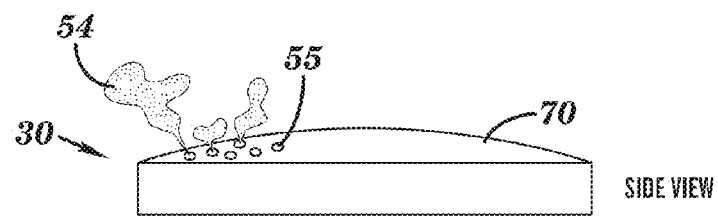
FIGS. 10A-10E are illustrations showing various embodiments of the ultrasound transducer of the present invention. These embodiments include ports 55 in the lens component 70 of transducer 30 that allow deliverable component 54 to pass therethrough.
Figure 10B:
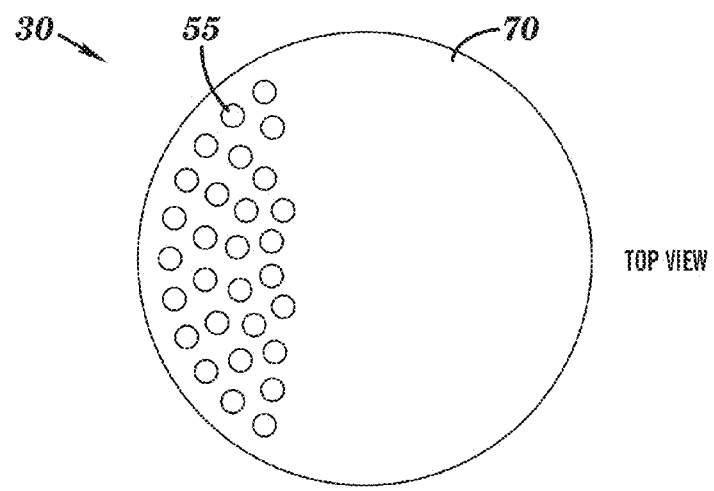
Figure 10C:
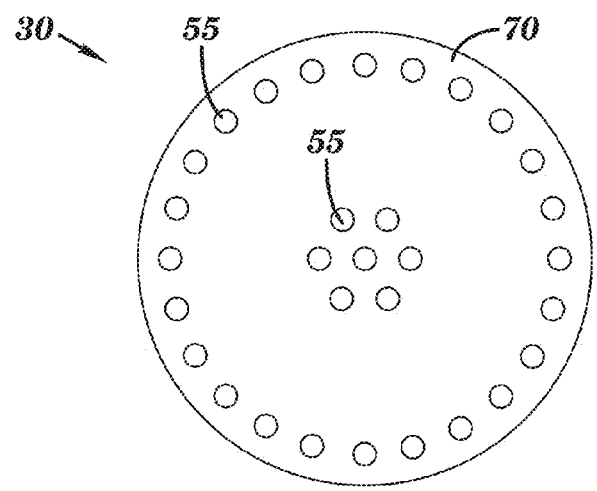
Figure 10D:
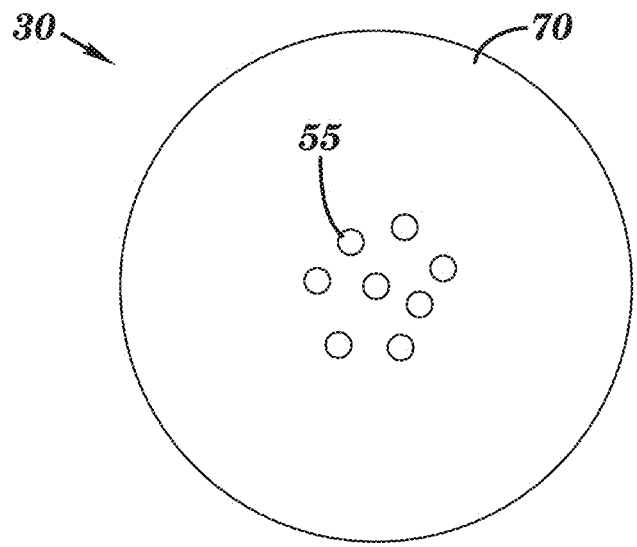
Figure 10E:
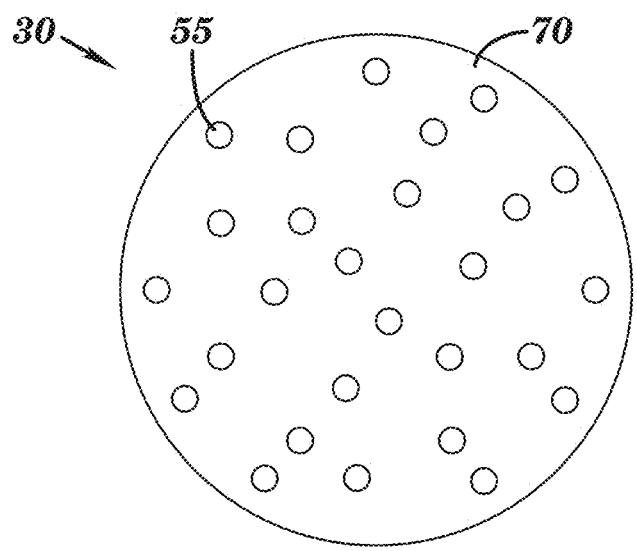

As shown in FIG. 9, piezoelectric component 60 includes front surface 61 and back surface 62. Front surface 61 is the portion of piezoelectric component 60 from which ultrasonic energy 35 is emitted or both ultrasonic energy 35 and light energy 52a are emitted. Back surface 62 is the portion of piezoelectric component 60 that is opposite to front surface 61.

As shown in FIGS. 10A-10E, lens component 70 can be configured to include a plurality of ports 55 through which deliverable component 54 can pass during ultrasound energy generation. Ports 55 can be of various sizes and arranged in various patterns. FIGS. 10A-10E are only provided as illustrative examples of the types of patterns and sizes of ports 55, but they are not being provided to limit the present invention only to those patterns depicted in the drawings. Deliverable component 54 can include any material that can pass through a hole or plurality of holes in piezoelectric component 60 in response to ultrasonic energy generated by portable ultrasound system 10. Thus, deliverable component 54 can be any ultrasound medium. Suitable examples of deliverable components 54 can include, without limitation, ultrasound gel, drugs, cosmetics, anti-bacterial compositions, disinfectants, lotions, etc., or a combination thereof. For example, deliverable component 54 can be in the form of a drug powder mixed into an ultrasound gel, or any other suitable ultrasound medium.

Figure 11A:
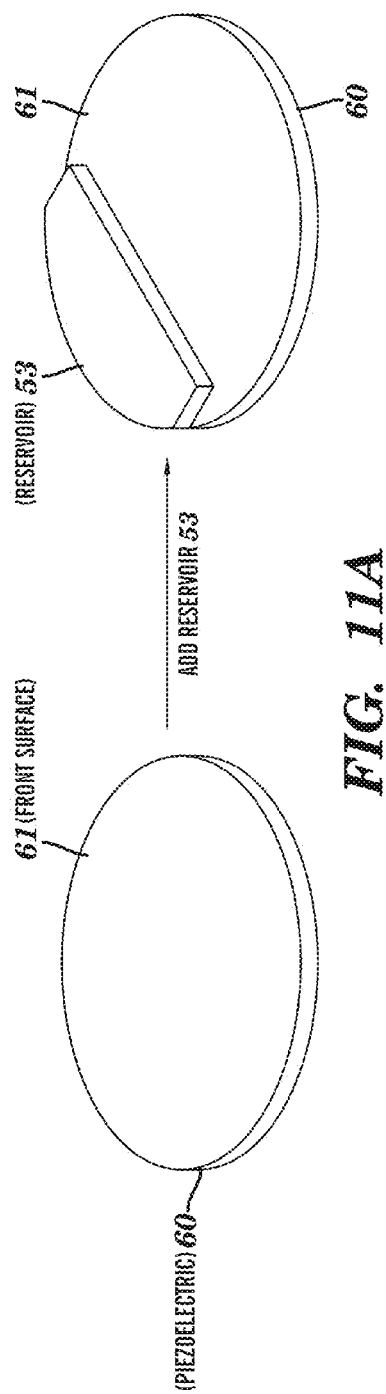
FIGS. 11A-11B are illustrations of perspective views of one embodiment of a piezoelectric component for use in the present invention. The piezoelectric component includes reservoir 53 attached to the front surface of the piezoelectric component.
Figure 11B:
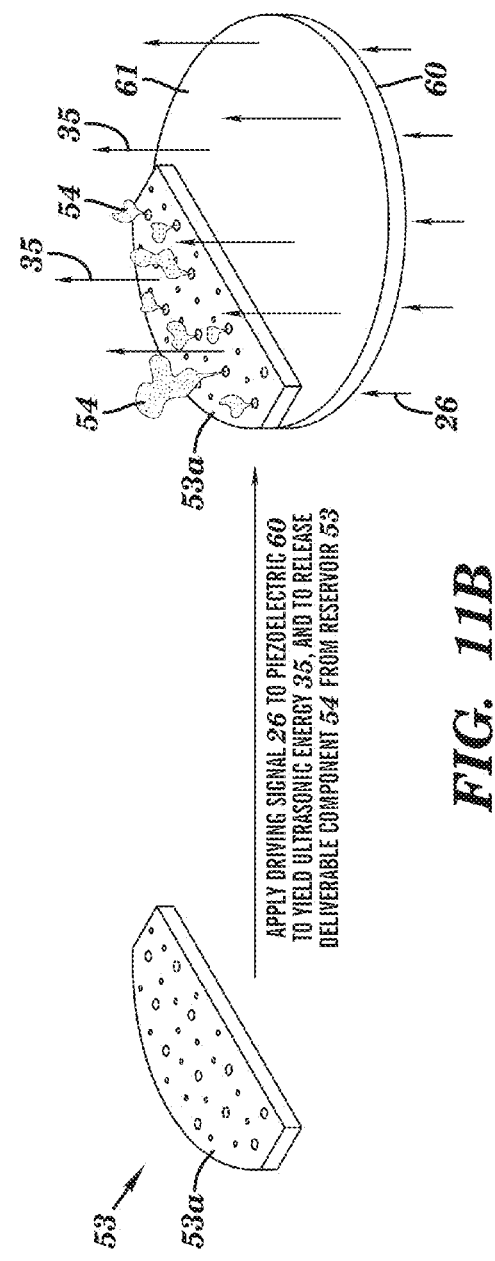

As shown in FIGS. 11A-11B, piezoelectric component 60 can further include reservoir 53 mounted to front surface 61 of piezoelectric component 60. Reservoir 53 is configured to store deliverable component 54 in the absence of ultrasound energy generation and to release deliverable component 54 in the presence of ultrasound energy generation. In one configuration, reservoir 53 forms a compartment attached to front surface 61 of piezoelectric component 60. As shown in FIG. 11B, in one embodiment, reservoir 53 can include a plurality of holes or other permeable or semi-permeable surface 53a to allow deliverable component 54 to pass therethrough. Lens component 70 can also be configured to include a plurality of holes or an otherwise permeable or semi-permeable region in order to allow deliverable component 54 exuded from reservoir 53 to pass through lens component 70 and to the surface of a subject.

The portable ultrasound system of the present invention is well suited for various types of assembly arrangements. The flexibility in assembly arrangements enables a wide range of applications, for human subjects as well as animal subjects (e.g., dogs, cats, horses, sheep, cows, swine, etc.). The assembly arrangement for animal subjects can differ as needed, primarily with respect to the type or configuration of the coupling device. Examples of suitable coupling devices can include such devices as Neoprene and Velcro wraps and the like, but others are contemplated for use with the present invention.

Figure 12A:
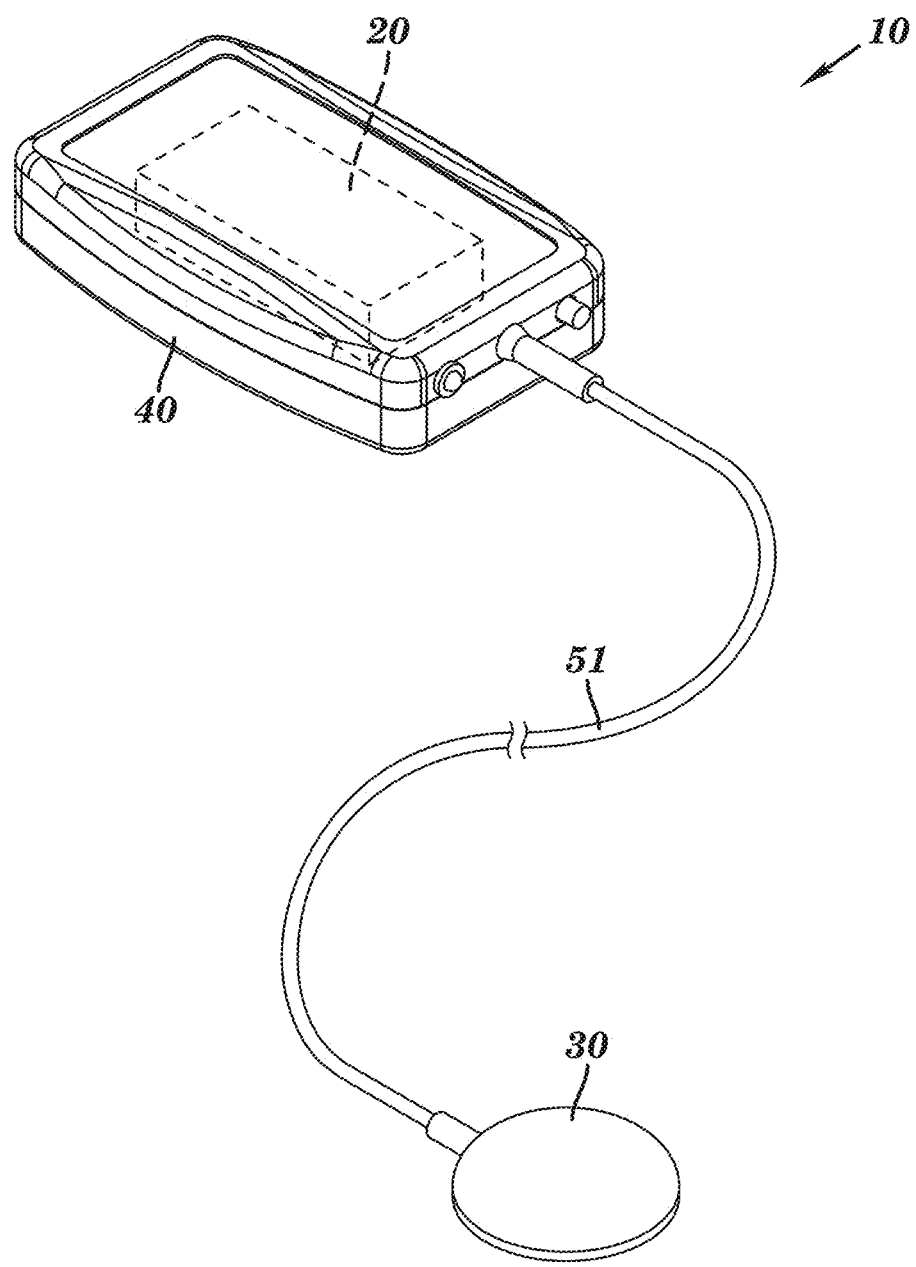
FIGS. 12A-12B show various embodiments of the portable ultrasound system of the present invention. In these embodiments, the transducer is connected to the energy generating module by a cable, with the energy generating module being contained in a housing 40.
Figure 12B:
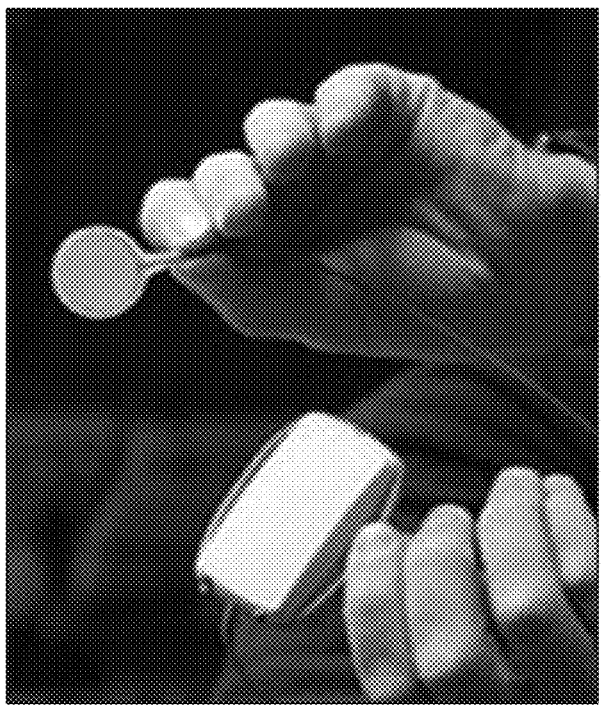

As shown in FIG. 12, portable ultrasound system 10 can be assembled so that energy generating module 20 is separate from ultrasound transducer 30. In this assembly arrangement, energy generating module 20 is completely housed in housing 40 and operatively coupled to ultrasound transducer 30 by cable 51. A suitable cable 51 can be any cable that is operative to allow the driving signal generated by energy generating module 20 to be delivered to ultrasound transducer 30 and emitted from ultrasound transducer 30 as ultrasonic energy 35. Examples of suitable cables 51 can include any wires suitable for the transducer and system used therewith, including, without limitation, flexible coaxial cables (e.g., Cooner Wire, NMEFI/2215044SJ) and the like.

Figure 13A:
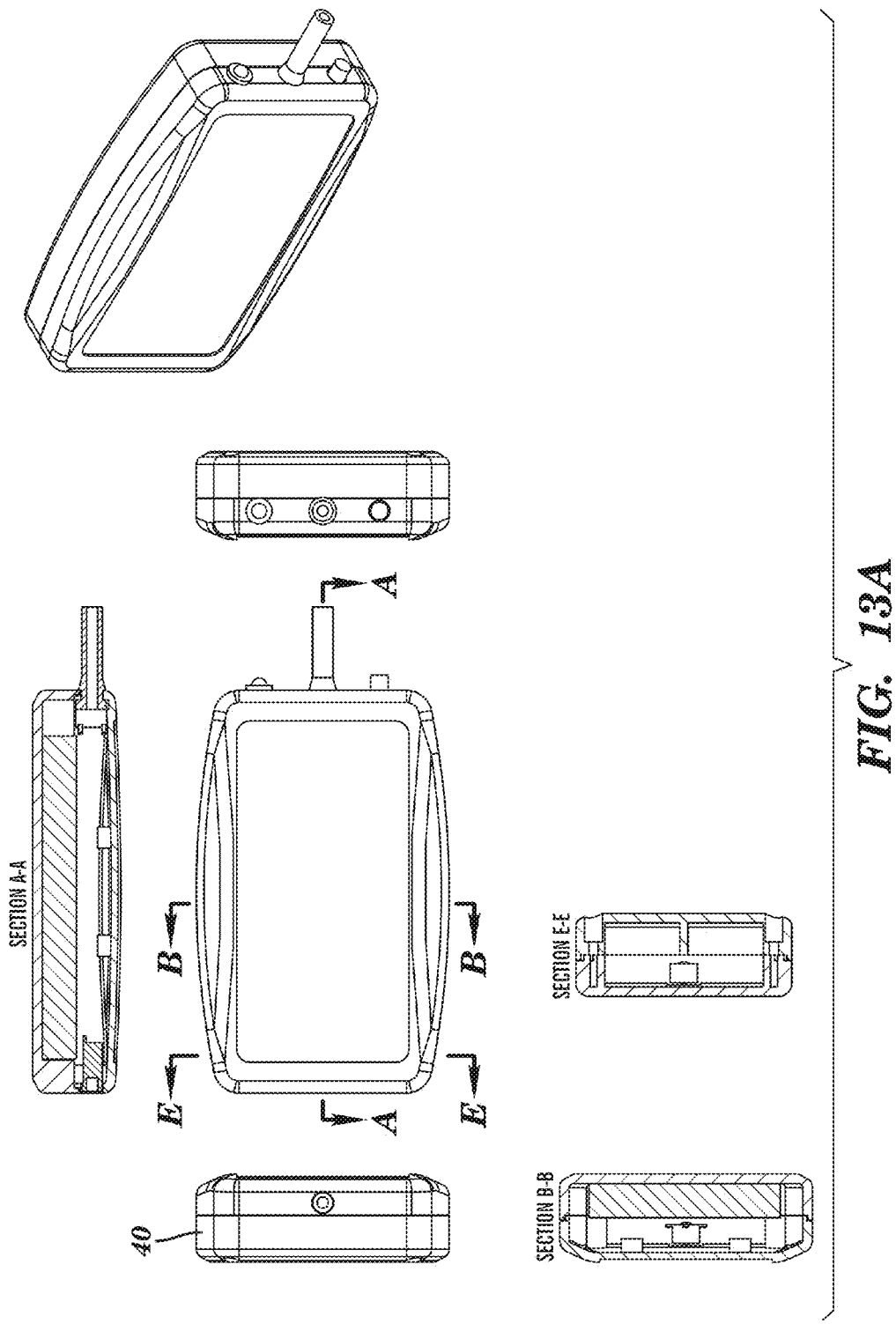

FIGS. 13A-13B illustrate aspects of one embodiment of housing 40 suitable for use with portable ultrasound system 10. Various materials can be used to make housing 40, including, for example, polycarbonate. As shown in FIGS. 13A-13B, in one embodiment, housing 40 can include two component halves that fit together to form a chamber suitable to house the energy generating module. One or more of the two component halves can include ports for a cable (e.g., to the ultrasound transducer), indicator light (e.g., indicating on/off), and an on/off switch (e.g., a toggle switch). Although dimensions of various portions of housing 40 are provided in FIGS. 13A-13B, the present invention is not limited to housings 40 having these dimensions. The dimensions can be configured according to the size and arrangement of the individual components of the energy generating module contained in housing 40.

Portable ultrasound system 10 can be assembled so that energy generating module 20 is at least partially housed on or within ultrasound transducer 30. In one embodiment of this assembly arrangement, oscillator 22 and driver component 23 are housed on or within ultrasound transducer 30, and power source 21 is housed in housing 40, with cable 51 operatively coupling power source 21 to oscillator 22/driver component 23 (housed on or within ultrasound transducer 30). In another embodiment, energy generating module 20 can further include voltage controller 24 operative to control power distribution from power source 21 to oscillator 22/driver component 23. In this embodiment, voltage controller 24 can either be housed in housing 40 along with power source 21 or housed on or within ultrasound transducer 30. As provided herein, voltage controller 24 can include on/off controller 24a coupled to transistor switch 24b.

Portable ultrasound system 10 can also be assembled so that energy generating module 20 is completely housed on or within ultrasound transducer 30. A suitable transducer can include, without limitation, the low-profile ultrasound transducer of the present invention.

The portable ultrasound system of the present invention is well suited for use with ultrasound transducers that are configured as low-profile type of ultrasound transducers. As used herein, the term "low-profile ultrasound transducer" is meant to include any ultrasound transducer that is configured to have a profile not greater than about 6 centimeters in height.

The portable ultrasound system of the present invention is also well suited for use with coupling devices designed for low-profile ultrasound transducers.

FIGS. 14, 15A-15B, 16A, 16B, 17, 18, 19, 20, 21, and 22 provide illustrative examples of suitable low-profile ultrasound transducers 50, or aspects thereof that can be used with portable ultrasound system 10. Suitable ultrasound coupling devices 100 that can be used with portable ultrasound system 10 and low-profile ultrasound transducers 50 are contemplated by the present invention to include any device that holds the system or transducer in place on any region of a subject, whether a human or animal subject.

Low-Profile Ultrasound Transducer

The present invention relates to a low-profile ultrasound transducer suitable for use with ultrasound systems, particularly portable ultrasound systems.

Figures 14A, 14B:
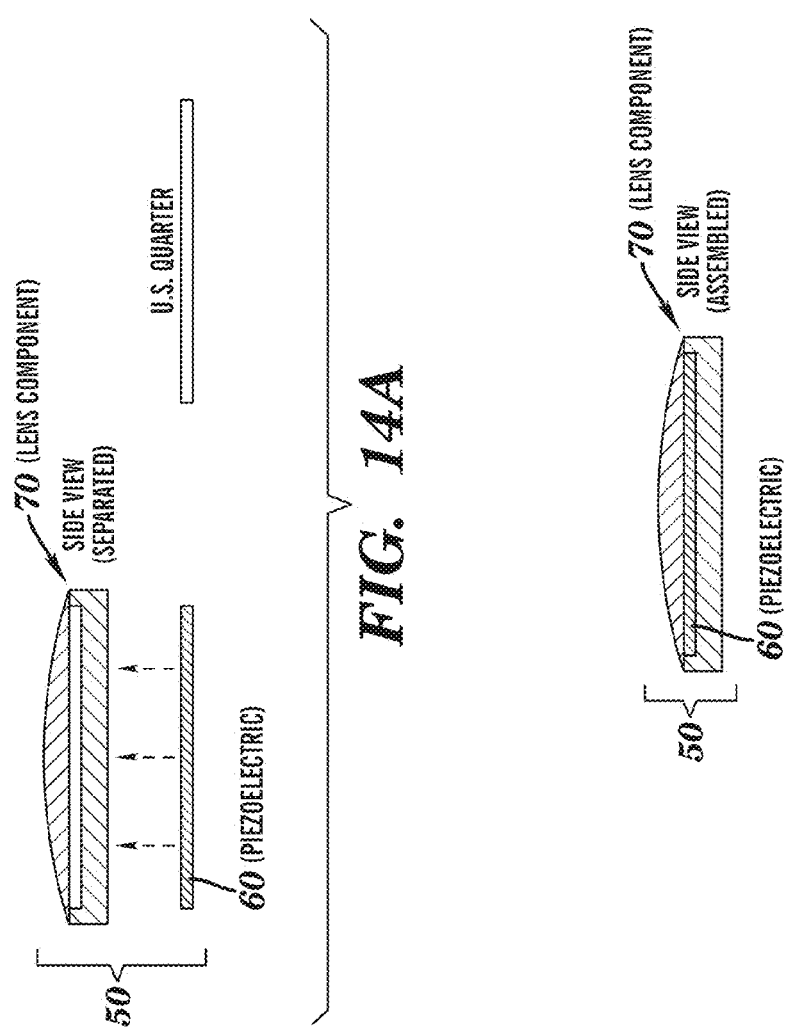
FIGS. 14A-14B are illustrations of one embodiment of a low-profile ultrasound transducer of the present invention.

FIGS. 14A-14B provide schematics of one embodiment of the low-profile ultrasound transducer of the present invention. As shown in FIGS. 14A-14B, low-profile ultrasound transducer 50 includes piezoelectric component 60 and lens component 70. FIGS. 14A-14B show ultrasound transducer 50 having lens component 70 that houses piezoelectric component 60 and that is configured as a single unit. FIG. 14A shows the various components prior to assembly. In this embodiment, piezoelectric component is a wafer disc about the size of a United States quarter dollar coin. FIG. 14B shows low-profile ultrasound transducer 50 fully assembled.

Piezoelectric component 60 is operative to receive a driving signal from energy generating module 20 and to emit the driving signal as ultrasonic energy 35. Piezoelectric component 60 is generally shaped as a disc having front surface 61 and back surface 62.

Piezoelectric component 60 is operative with an energy generating module 20 having a plurality of electronic components 26. In one embodiment, the plurality of electronic components 26 of energy generating module 20 includes power source 21, oscillator 22, and driver component 23. In another embodiment, the plurality of electronic components 26 of energy generating module 20 can further include temperature sensor 25 and/or wireless recharger component 90. Other suitable electronic components useful in ultrasound circuitry are contemplated by the present invention. Piezoelectric component 60 is effective to transmit ultrasonic energy having an acoustic intensity ranging from between about 10 mW/cm$^2$ and about 5 W/cm$^2$.

Figure 15A:
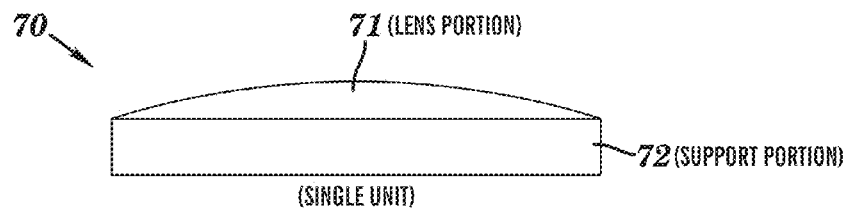
FIGS. 15A-15B are illustrations of one embodiment of a lens component of a low-profile ultrasound transducer of the present invention.
Figure 15B:
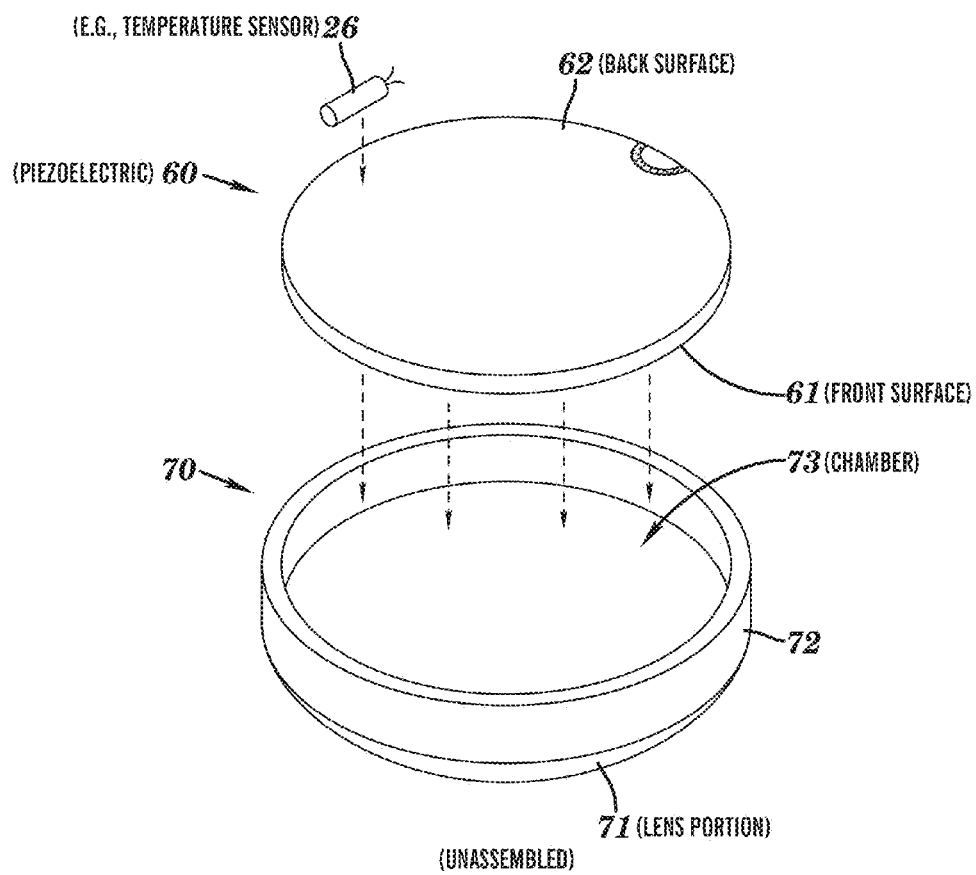

As shown in FIGS. 15A-15B, lens component 70 includes lens portion 71 and support portion 72. Lens component 70 can be directly or indirectly deposited on front surface 61 of piezoelectric component 60. Lens portion 71 of lens component 70 is configured to control the direction and wave pattern of ultrasonic energy 35 emitted from piezoelectric component 60. Support portion 72 of lens component 70 is also configured to hold piezoelectric component 60 in place and to provide chamber 73 for housing at least one electronic component 26 of energy generating module 20.

As shown in FIGS. 5A, 5B, 6A, and 6B, lens portion 72 can be configured to emit ultrasonic energy 35 in various wave patterns, including, for example, diverging wave pattern 35a, scattering wave pattern 35b, focused wave pattern 35c, or parallel wave pattern 35d. In one embodiment, lens portion 71 can be convex lens 74 configured to emit the ultrasonic energy in diverging wave pattern 35a. In another embodiment, lens portion 71 can be ridged lens 75 configured to emit the ultrasonic energy in scattering wave pattern 35b. The lens may be used to direct energy into joints where the transducer may not be easily positioned over. The lens can be used to control the distribution of ultrasound energy. The lens can be used to form ultrasound standing waves in the body. The lens can also be used to prevent standing wave formation in the body. The lens can be used to generate random acoustic field patterns.

Lens component 70 is effective to spread ultrasonic energy emitted from piezoelectric component 60 for ultrasound therapy from an angle ranging from between about 0 degrees and about 180 degrees.

Figure 16B:
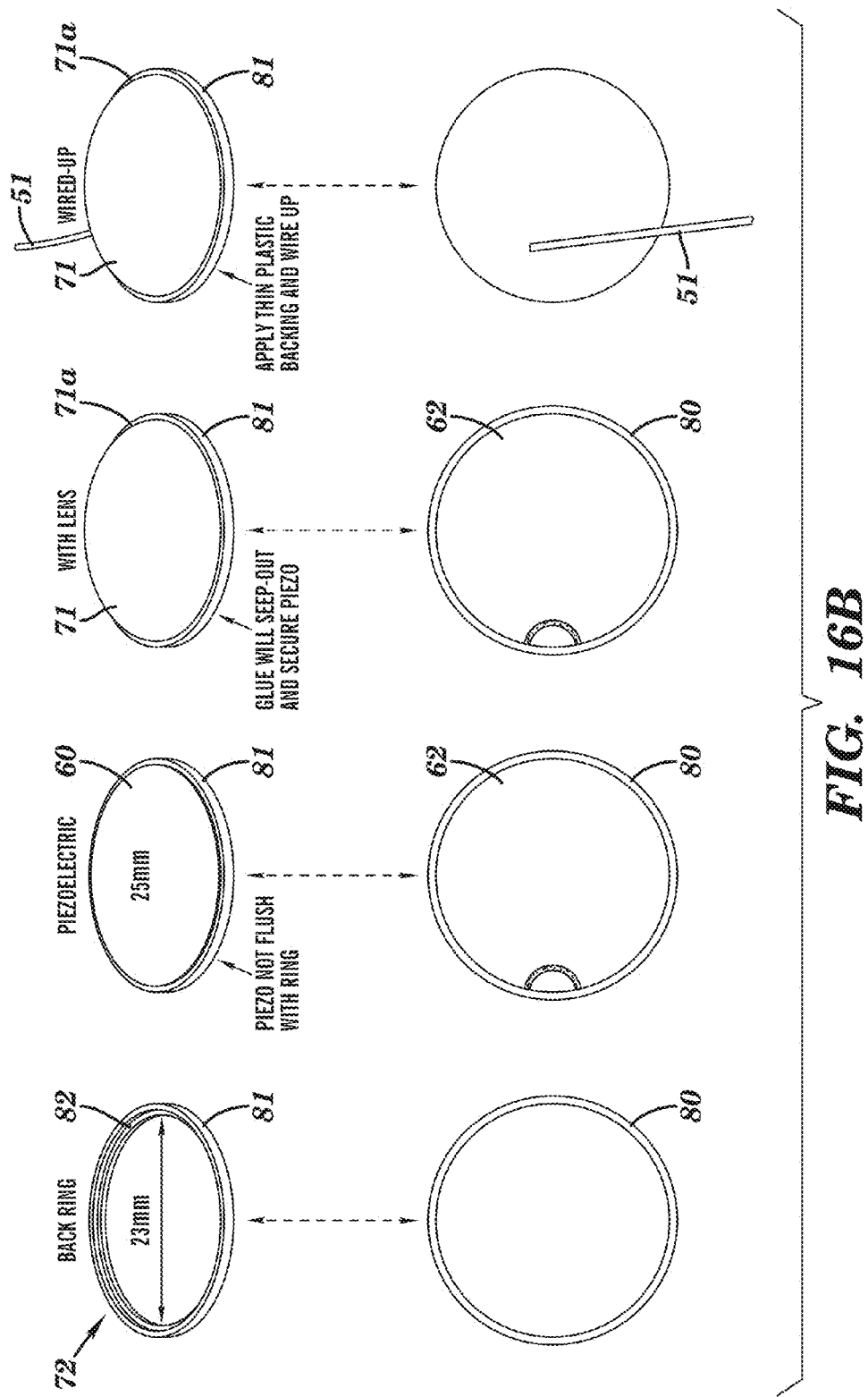

As shown in FIGS. 16A-16B, in one embodiment, support portion 72 is configured as a ring 80 having outer ring portion 81 and inner ring portion 82, with inner ring portion 82 forming a ring-like shelf within outer ring portion 81 effective to hold piezoelectric component 60 in place.

Figure 17:
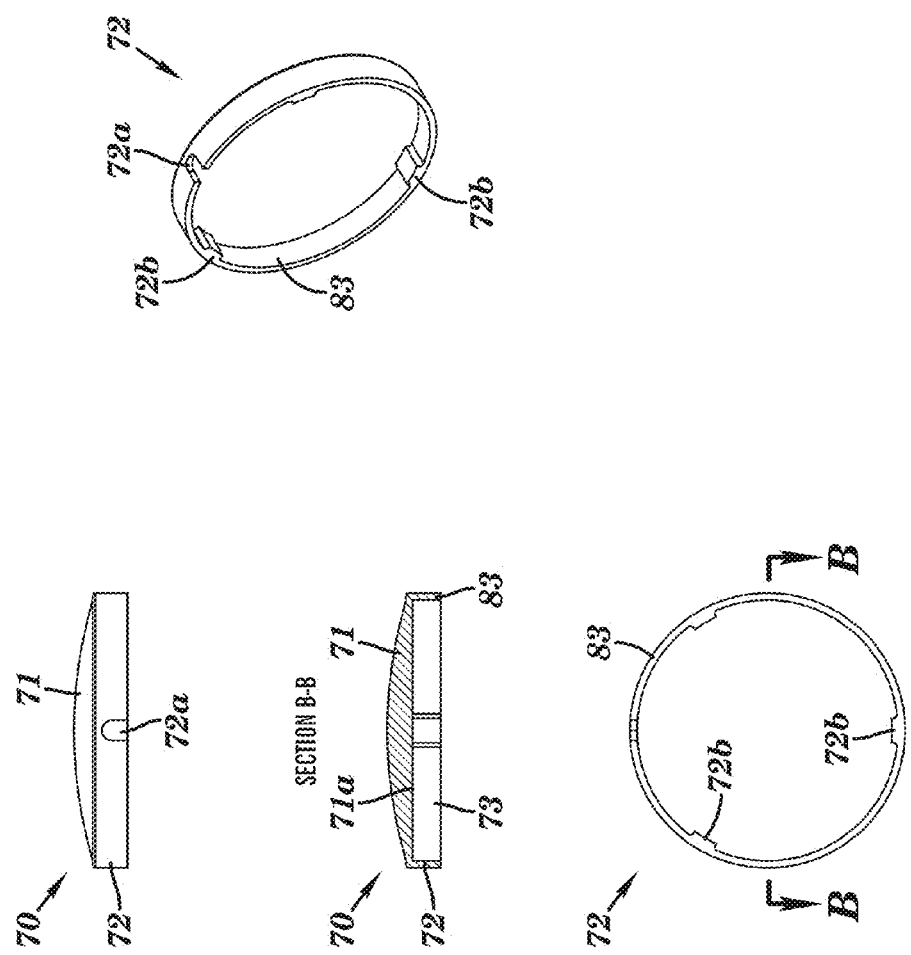
FIG. 17 are illustrations of one embodiment of a lens component 70 of a low-profile ultrasound transducer of the present invention. The lens component includes lens portion 71 and support portion 72 combined as a single unit. Although dimensions for the lens component are shown, these are for illustrative purposes only and are not meant to limit all such lens components of the present invention to these dimensions.

As shown in FIG. 17, in one embodiment, lens portion 71 and support portion 72 form a single lens component 70. In this embodiment, lens portion 71 forms a front end base portion 71a of chamber 73, and support portion 72 forms support wall 83 of chamber 73. As shown, support wall 83 extends in a backward direction from front end base portion 71a. Support portion 72 can further include opening 72a, which can be used as a passage way for a cable that connects the piezoelectric component or other electronic component to another electronic component disposed outside of chamber 73 (e.g., a power source connected by a cable). In addition, as shown in FIG. 17, one embodiment of lens component 70 can be configured to include notches 72b as part of the inner surface of support wall 83. Notches 72b function to position piezoelectric component 60 within chamber 73 in a manner well-suited for attaching piezoelectric component 60 to front end base portion 71a of chamber 73.

As shown in FIG. 17, in one embodiment, three notches 72b can be included as part of the inner surface of support wall 83. In assembling the low-profile ultrasound transducer of the present invention, glue or another suitable adhesive is used to secure piezoelectric component 60 in place on front end base portion 71a.

First, glue is applied to front end base portion 71a or alternatively to front surface 61 of piezoelectric component 60, or to both. Piezoelectric component 60 is then placed within chamber 73 so that it comes in contact with front end base portion 71a, with the glue layer being disposed between piezoelectric component 60 and front end base portion 71a. Notches 72b position piezoelectric component 60 so that there is space between the outer edges of piezoelectric component and the inner surface of support wall 83. In turn, this space allows for excess glue and air bubbles contained in the glue to be exuded from between the contact point of piezoelectric component 60 and front end base portion 71a and into the space, thereby allowing a functionally sufficient and efficient contact between piezoelectric component 60 and lens portion 71. Although FIG. 17 shows an embodiment having three notches 72b, the present invention is not limited to three notches 72b, but includes embodiments having other arrangements, as long as an adequate space for exuding excess glue and air bubbles is provided.

Figure 18:
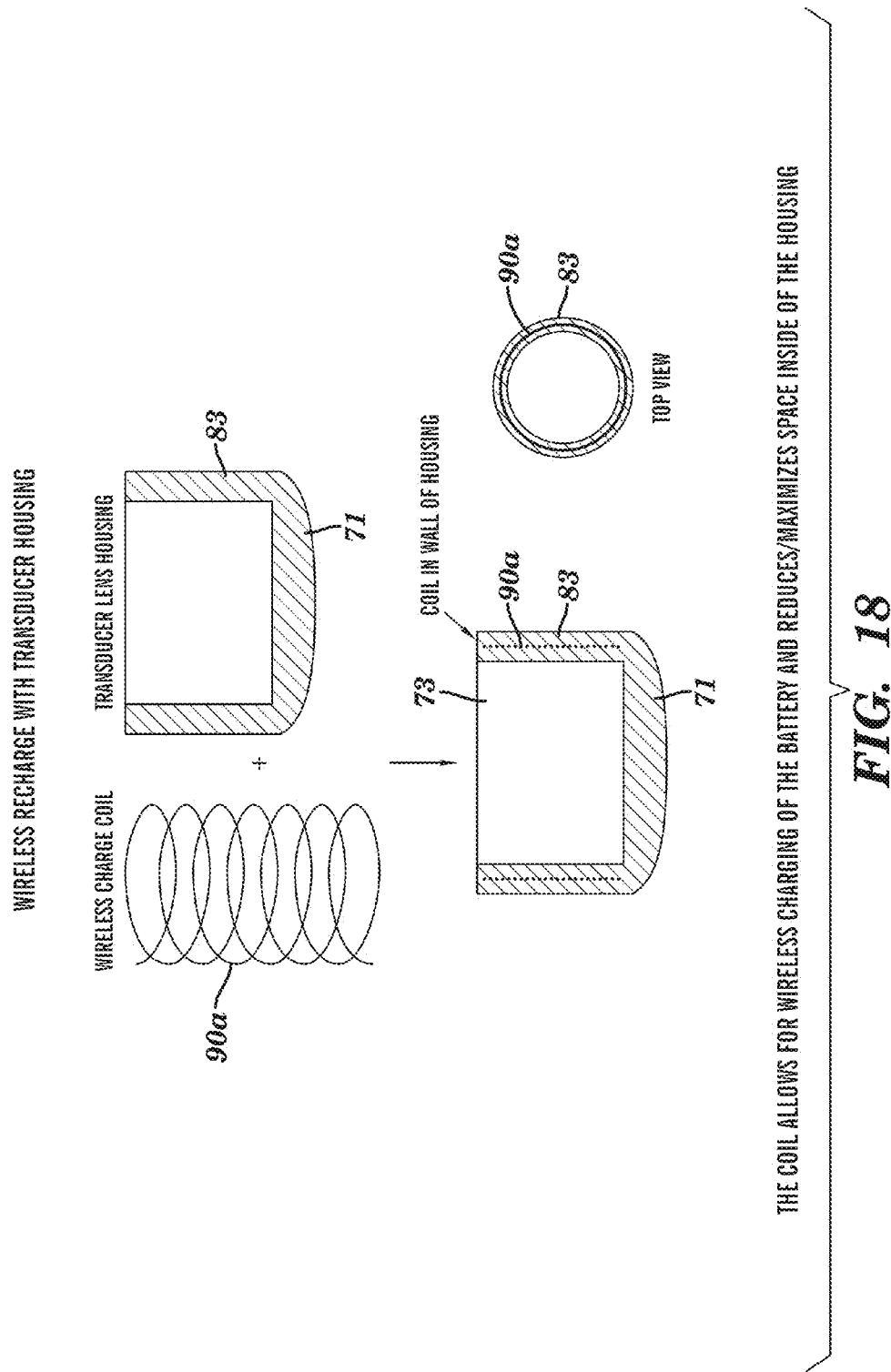
FIG. 18 shows one embodiment of a lens component of a low-profile ultrasound transducer of the present invention. The lens component is shown to include a wireless recharger coil 90a in the support wall 83 of lens component. Side and top views are shown.

As shown in FIG. 18, in one embodiment, support wall 83 can be configured to include wireless recharger coil 90a. Suitable wireless recharger coils 90a can include, without limitation, wire rings, inductive coupling, and the like. Wireless recharger coils 90a are used in embodiments that use rechargeable batteries. The coil in the wall maximizes the inductive-charging capability because it allows for the electrical field pass through the center of the coil. The coil in the wall also maintains the low profile of the device.

The coil does not have to be in the housing wall. For example, the coil could be in the inside of the transducer, in the case of the system or on the outside of the transducer in the coupling device (e.g., a rubber boot), in the coupling device (e.g., rubber boot), or in-between the case and the rubber boot.

Figure 19:
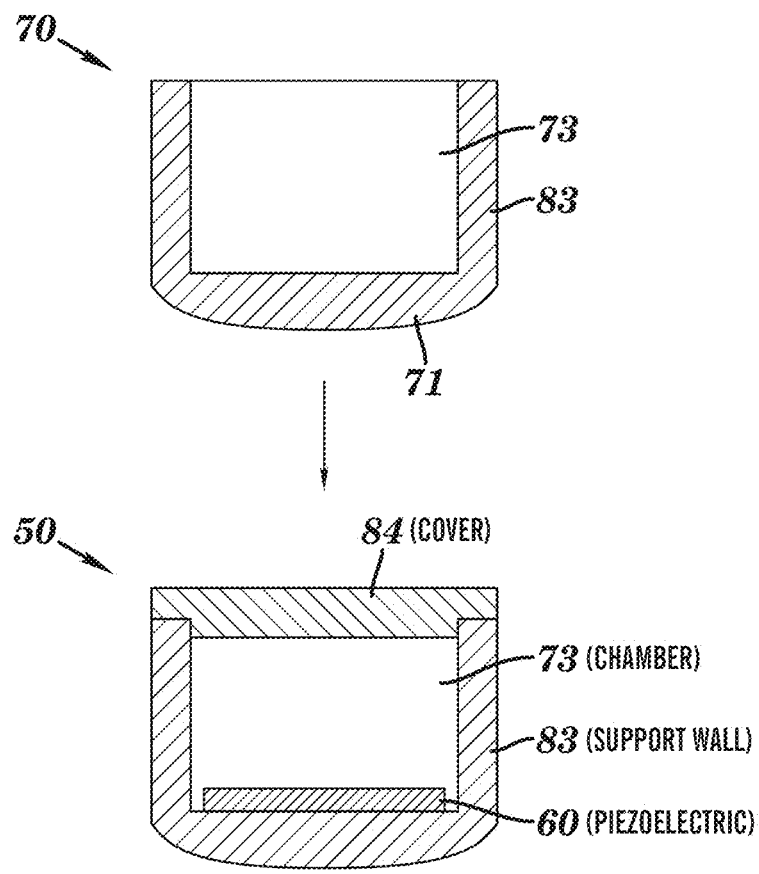
FIG. 19 shows a cross-sectional view of one embodiment of a low-profile ultrasound transducer of the present invention assembled to include lens component 50 as a single unit, piezoelectric component 60 deposited within chamber 73, and cover 84 covering support wall 83.

As shown in FIG. 19, low-profile ultrasound transducer 50 can be configured to also include cover 84. Cover 84 is deposited over support wall 83 in a manner effective to substantially close chamber 73. This embodiment is useful to protect any electronic components 26 contained within chamber 73.

Figure 20:
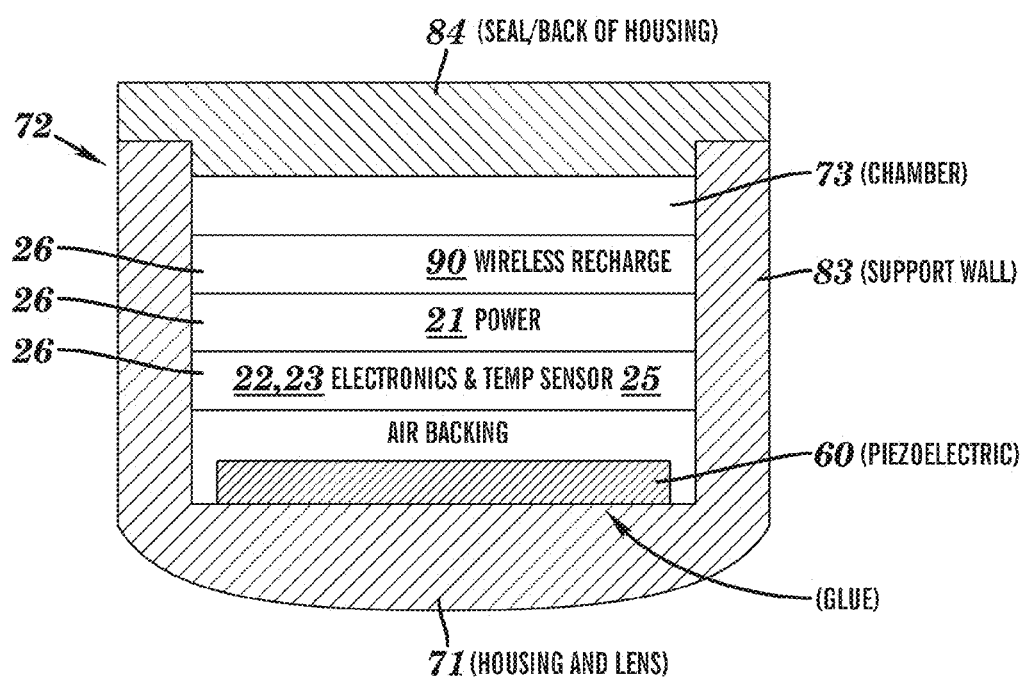
FIG. 20 shows a cross-sectional view of one embodiment of a low-profile ultrasound transducer of the present invention. The transducer is configured to include power source 21, electronic components 26, and piezoelectric component 60 within chamber 73. Piezoelectric component 60 is attached to lens portion 71 by glue and is separated from the other components contained within chamber 73 by air backing. In an alternative embodiment, a temperature sensor 25 can be directly deposited on the back surface of piezoelectric component 60, or nearby piezoelectric component 60.

Embodiments having the lens portion and the support portion forming a single lens component are well suited for housing electronic components of the energy generating module. For example, as shown in FIG. 20, chamber 73 can house piezoelectric component 60 in addition to at least one electronic component 26 of energy generating module 20. Electronic components 26 housed in chamber 73 can include one or more of the following: power source 21, oscillator 22, driver component 23, temperature sensor 25, and wireless recharger component 90.

Figure 21:
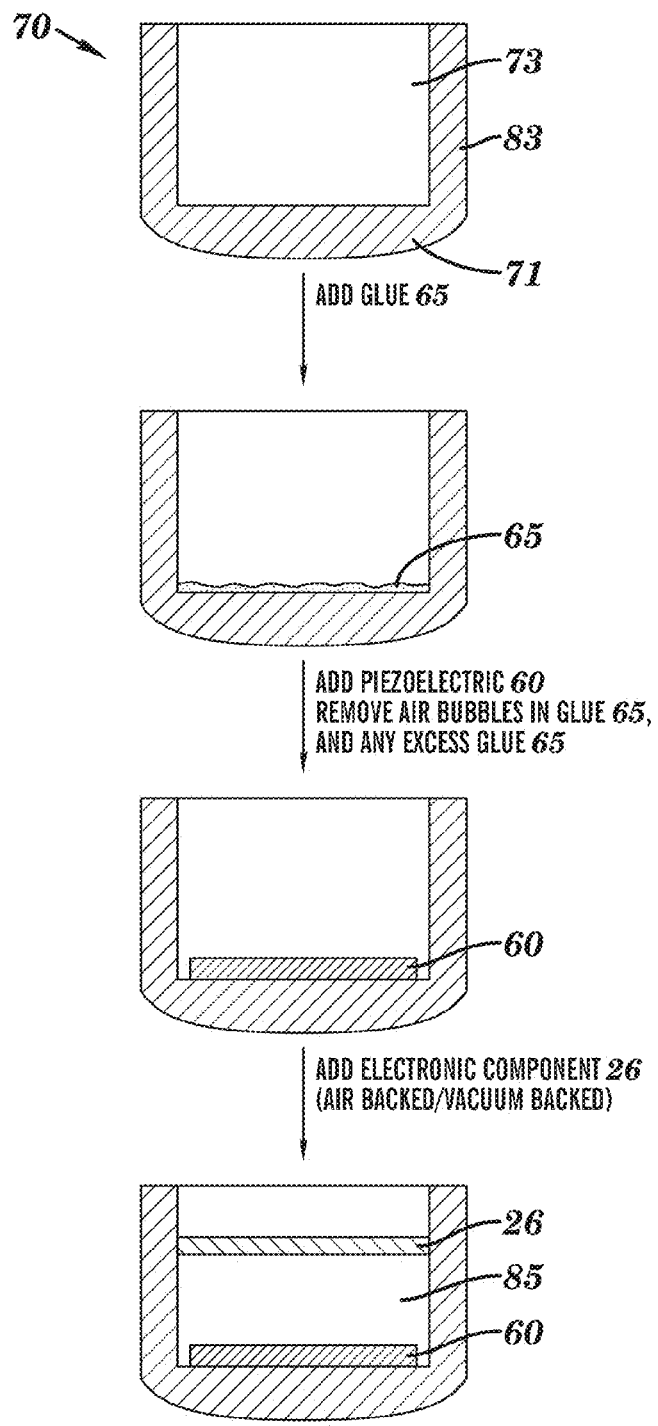
FIG. 21 illustrates the assembly of one embodiment of a low-profile ultrasound transducer of the present invention. The assembly procedure illustrates the placement of piezoelectric component 60, vacuum backing, and placement of an electronic component 26.

As shown in FIG. 21, in one embodiment, the one or more electronic components 26 are housed in chamber 73 so as to be separated from piezoelectric component 60 by layer of air 85. This can be achieved using various techniques know in the electronics field. Examples of such techniques can include air backing or vacuum backing techniques known in the art. In a particular technique, the piezoelectric component is air backed or vacuum backed to increase ultrasonic energy propagation in a forward direction.

In one embodiment, at least one electronic component can be either mounted onto the piezoelectric component or deposited near but not onto the piezoelectric component. As shown in FIG. 22, for this embodiment, temperature sensor 25 is well suited for being the only electronic component to be mounted onto piezoelectric component 60 or deposited near but not onto piezoelectric component 60. Temperature sensor 25 is useful in detecting the heat level and in trigger a shutdown of power when the heat level rises to a predetermined level. Suitable temperature sensors can include, for example, thermal cutoffs, remote temp sensing ICs, and local temp sensing ICs.

Another aspect of the low-profile ultrasound transducer of the present invention relates to the use of the transducer in both generating ultrasonic energy and light energy. These embodiments of the low-profile ultrasound transducer include at least one light source operative to generate light energy from the driving signal provided by the energy generating module. Such embodiments enable a variety of applications that benefit from both ultrasonic energy therapy and light therapy, or that use light energy to provide signaling or decorative lighting. The light source can be wired to a front conductor of the piezoelectric component and a back conductor of the piezoelectric component, thereby allowing the driving signal to the piezoelectric component to power the light source. Alternatively, the light source can be wired around the piezoelectric component or through the piezoelectric component. Further, the light source can be configured to be powered either in series or in parallel with the piezoelectric component. Also, the light source can be generated either from the piezo generator or from a separate external generator.

Figure 23:
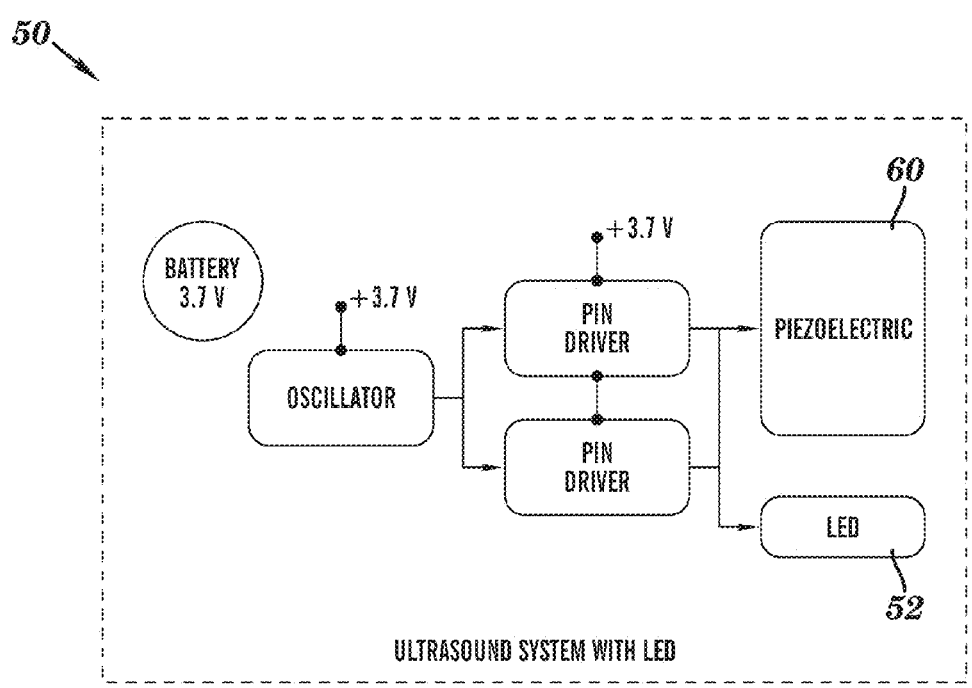
FIG. 23 is a schematic of one embodiment of a low-profile ultrasound transducer of the present invention. This embodiment includes light source 52 (e.g., LED).
Figure 24:
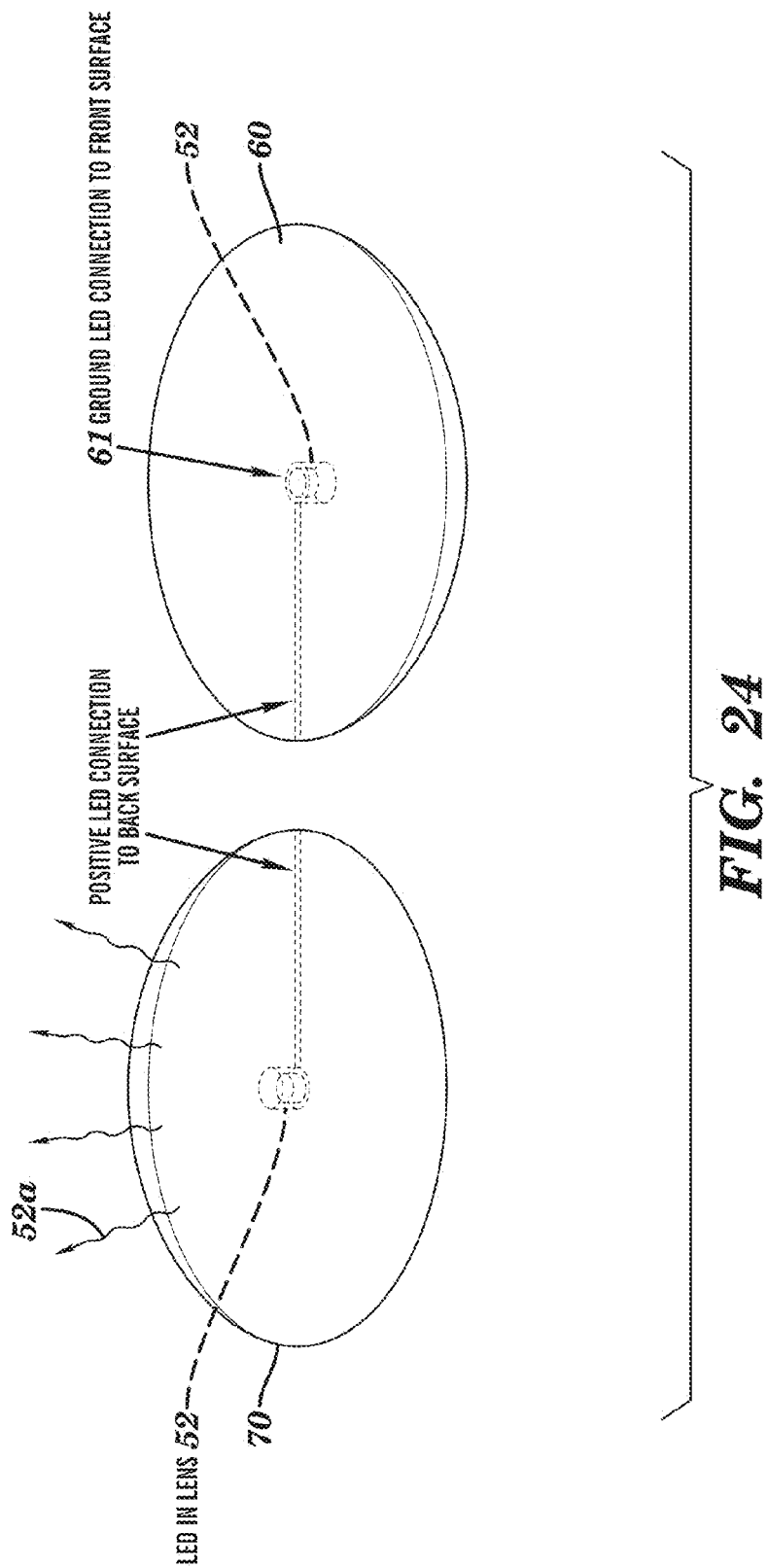
FIG. 24 shows one embodiment of a low-profile ultrasound transducer of the present invention having a lens component 70 that is configured to allow light energy 52a (depicted as wavy arrows) to pass therethrough.

As shown in FIG. 23, low-profile ultrasound transducer 50 can be configured to include light source 52 or a plurality of light sources 52 securely deposited in proximity to piezoelectric component 60 and/or lens component 70. Suitable light sources can include any light source that can run on the power source of the present invention. For example, in various embodiments, the light source can be a light-emitting diode (LED), a laser, or a combination thereof. As shown in FIG. 24, lens component 70 can be configured to be operative to allow light energy 52a to pass through it. As shown, light energy 52a is emitted through lens component 70 through front surface 61 of piezoelectric component 60.

Figure 25:
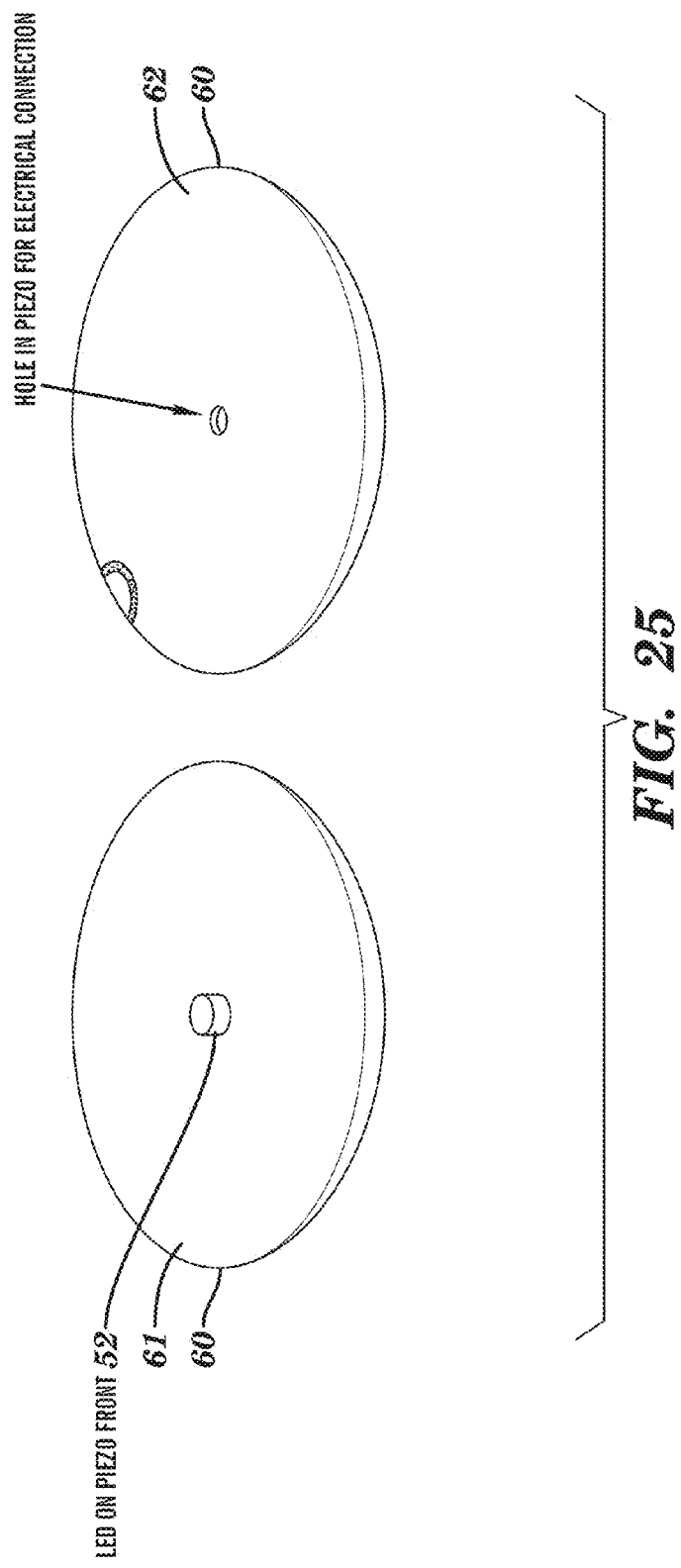
FIG. 25 is shows one embodiment of a piezoelectric component 60 of a low-profile ultrasound transducer of the present invention. The piezoelectric component is configured to have a light source disposed therein.

As shown in FIGS. 24-25, in one embodiment, light source 52 can be configured to be set inside of lens component 70, inside piezoelectric component 60, or inside both lens component 70 and piezoelectric component 60.

As shown in FIG. 24, in one embodiment, light source 52 can be configured to be set substantially in the center of lens component 70, piezoelectric component 60, or both lens component 70 and piezoelectric component 60.

The low-profile ultrasound transducer of the present invention can be integrated into a portable ultrasound system, including portable ultrasound systems that include an energy generating module, where the energy generating module includes a power source, an oscillator, and a driver component coupled to the transducer. The energy generating module can either be housed within or not housed within the low-profile ultrasound transducer.

The present invention also relates to a multi-unit transducer that includes a plurality of the ultrasound transducers combined into a single multi-unit transducer, with at least one of the transducers being a low-profile transducer described herein. The plurality of ultrasound transducers can include transducers of either the same or different functions and/or sizes, and can emit the same or different intensity, duration, or frequency of ultrasonic energy or light energy.

The low-profile ultrasound transducer of the present invention can be made as follows: (i) providing a piezoelectric component operative to receive a driving signal from an energy generating module and to emit the driving signal as ultrasonic energy, said piezoelectric component having a front surface and a back surface, and said energy generating module comprising a plurality of electronic components; (ii) providing a lens component said lens component comprising a lens portion and a support portion; and (iii) directly or indirectly depositing the lens component on the front surface of the piezoelectric component, wherein the lens portion of the lens component is configured to control the direction and wave pattern of the ultrasonic energy emitted from the piezoelectric component, and wherein the support portion of the lens component is configured to hold the piezoelectric component in place and to provide a chamber for housing at least one electronic component of the energy generating module.

Based on the illustrative figures and discussion contained herein, one of ordinary skill in the art would be able to assemble the low-profile ultrasound transducer. For example, in one assembly process, the lens and housing are combined into one piece so that the piezoelectric is dropped in and glued into place. A heat sensor can be soldered to the back of the piezoelectric. The casing backplate can then be glued to seal the air backed portion of the piezoelectric. The circuitry and power source can also be placed into the transducer housing. Further, with respect to the portable ultrasound system and the low-profile ultrasound transducer of the present invention, Application Specific Integrated Circuit (ASIC) technology can be employed.

Figure 26:
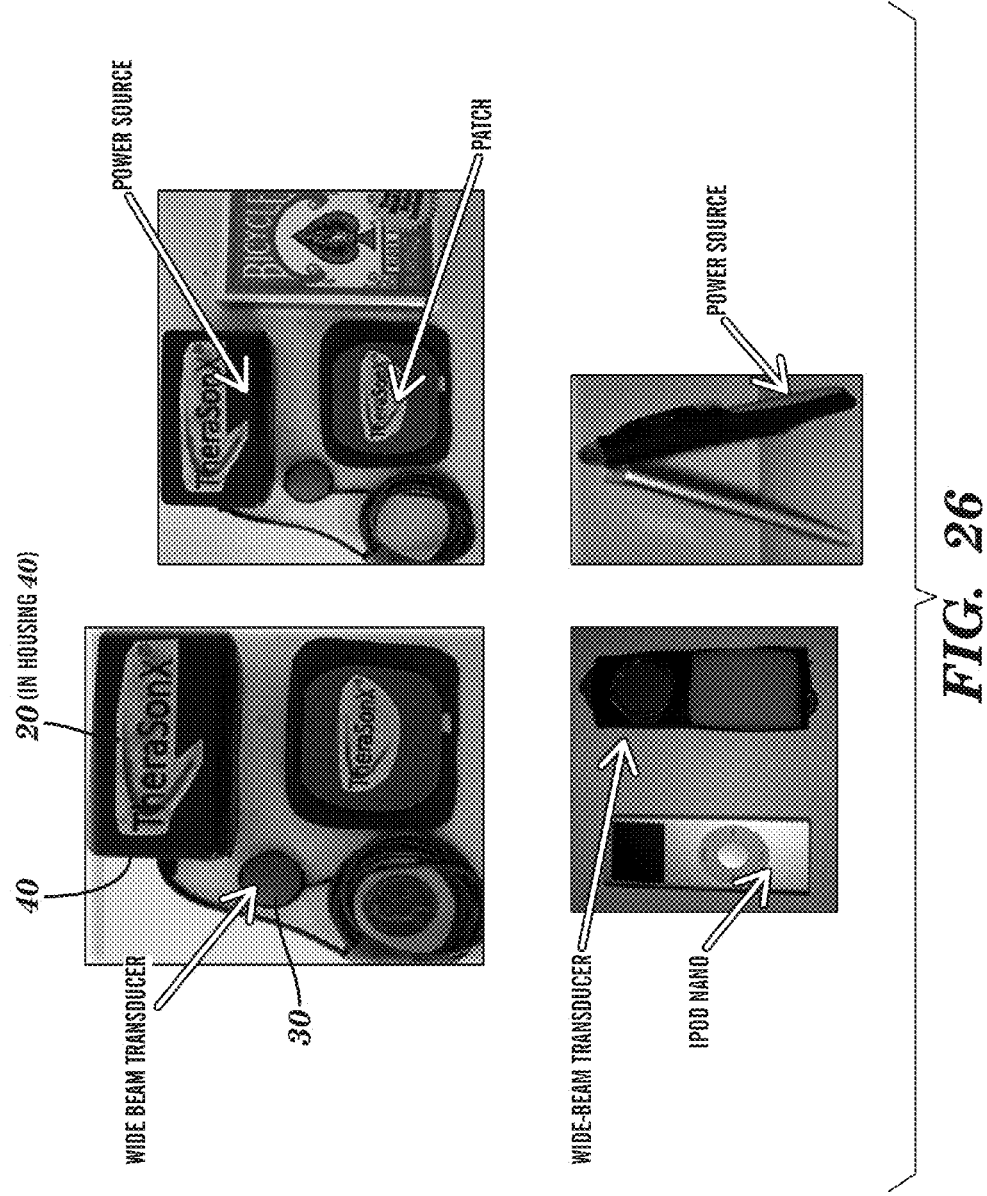
FIG. 26 are photographs showing embodiments of portable ultrasound systems according to the present invention. Well known objects are included to illustrate the relative size of these embodiments.

FIG. 26 is a photograph showing various embodiments of the ultrasound transducer of the present invention. Various well known objects (e.g., a United States quarter dollar coin, a pack of playing cards, and an Apple iPOD Nano) are also provided in FIG. 26 in order to illustrate the relative size of the depicted portable ultrasound system/low-profile ultrasound transducer of the present invention.

Figure 27:
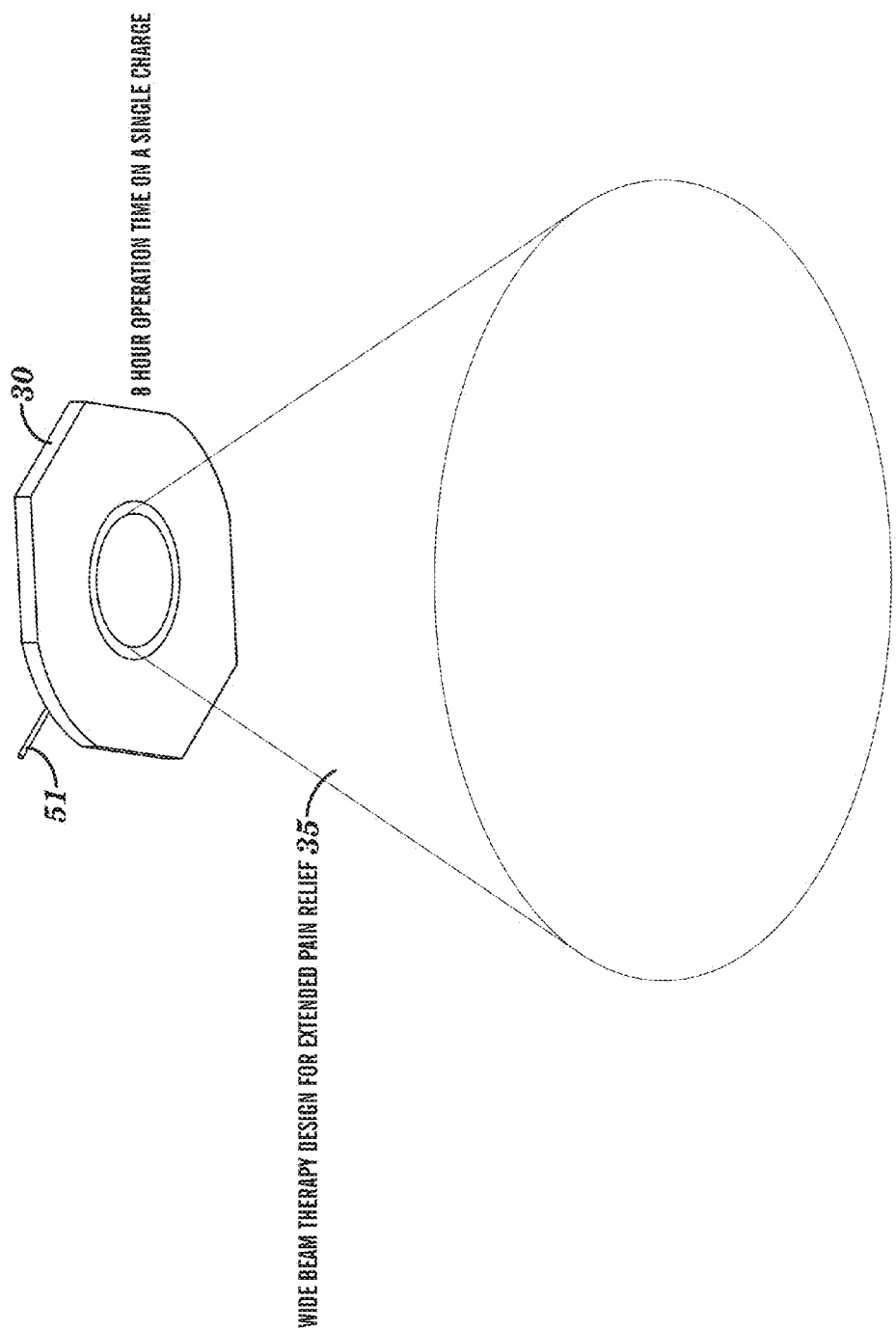
FIG. 27 is an illustration showing wide-beam therapeutic ultrasound emitted from ultrasound transducer 30.

The low-profile ultrasound transducer and the ultrasound system of the present invention are operative in producing a wide range of ultrasonic beams and wave patterns, enabling a wide range of applications. As shown in FIG. 27, a particular embodiment produces ultrasonic energy 35 in the form of a wide-beam that can be used for extended pain relief. For example, the ultrasound system can operate for 8 hours on a single charge.

As shown in FIGS. 28A, 28B, and 28C, the low-profile ultrasound transducer and the ultrasound system of the present invention can be used for a number of applications. FIG. 28A shows the use of the system and transducer for treating joints of the fingers. In this embodiment, the lens can be configured to direct the ultrasonic energy to the area of interest on and within the tissue of the subject near and at the joint. FIG. 28B shows the use of the system and transducer for treating the arm of a subject. As shown in FIG. 28B, a hydrogel component can be used in tandem with the transducer as an ultrasound conductive medium. The hydrogel component can be configured to fit the shape of the transducer and lens in order to couple ultrasonic energy into the body (e.g., into the arm tissue) of a subject. FIG. 28C shows the use of multiple systems in an array. For example, as shown in the embodiment of FIG. 28C, a plurality of ultrasound transducers/systems of the present invention can be coupled with a holder component 900 (shown as a multi-unit holder component 902). In this application, holder component 900 can be in the form of a Neoprene wrap and used to treat a large area such as the lower back (as shown).

Methods of Use

The present invention further relates to various methods of using the portable ultrasound system and the low-profile ultrasound transducer of the present invention. The basic use involves applying ultrasonic energy to a subject, whether human or animal, at a target area using the portable ultrasound system and/or the low-profile ultrasound transducer of the present invention. The length of time and intensity can be based on industry standards. Some uses can be found at www.ultroz.com. Below is a brief description of certain uses of the portable ultrasound system and the low-profile ultrasound transducer of the present invention.

In one application, the present invention relates to a method for performing physiotherapy on a subject. This method involves providing a portable ultrasound system of the present invention or a plurality of the systems in the form of an array, and then applying therapeutic ultrasound energy to a target area of a subject, where the therapeutic ultrasound energy is generated by the system or array of systems.

In another application, the present invention relates to a method for applying ultrasound energy to a subject. This method involves providing a portable ultrasound system of the present invention or a plurality of the systems in the form of an array, and applying ultrasound energy to a target surface of a subject, where the ultrasound energy is generated by the system or array of systems.

In another application, the present invention relates to a method of topically delivering a drug to a subject. This method involves providing a portable ultrasound system of the present invention or a plurality of the systems in the form of an array, where the deliverable component includes a drug to be delivered to a subject, and applying ultrasound energy to a surface of a subject along with the deliverable component, where the ultrasound energy is generated by the system or array of systems.

In another application, the present invention relates to a method of internally delivering a drug to a subject. This method involves administering to a subject a biocompatible device of the present invention, where the biocompatible component is in the form of an ingestible device that includes a drug to be delivered to the subject, and where the device is effective to generate ultrasound energy in order to facilitate internal delivery of the drug to the subject.

The portable ultrasound system and low-profile ultrasound transducer of the present invention have various attributes, as described herein and as further discussed below.

For example, the ultrasound power source and circuit are such that they can be mounted directly onto the ultrasound transducer (e.g., the piezoelectric component). Thus, in one embodiment, the complete ultrasound system of the present invention can be as small as a stack of approximately 2-3 U.S. quarters.

In a particular embodiment, the ultrasound producing circuit used in the system of the present invention can include two components: (i) an oscillator to control the frequency of the device; and (ii) two pin drivers in parallel to drive the transducer, although as few as one pin driver could be used.

Another optional component of the ultrasound system of the present invention can be a light-emitting diode (LED) or a plurality of LEDs, which may be arranged around the ultrasound transducer to provide "light" therapy. The LEDs can be powered from the same ultrasound producing circuit that powers the ultrasound transducer.

The power source used to power the device may be any source of power suitable for generating the necessary power to run the ultrasound system according to its intended use. By way of example only, a particular suitable power source that can be used to power the device may include, without limitation, batteries such as coin lithium ion watch batteries and the like.

As noted herein, one embodiment of the ultrasound producing system of the present invention can include a piezoelectric, ultrasound generating circuit, and power supply. Additional features may include power control (On/Off), LED's, lenses, and recharging capability. One advantageous aspect of this invention is that the complete ultrasound device may be made in the size and shape of a U.S. quarter or even smaller (e.g., an ingestible pill).

Without meaning to limit the present invention to a particular embodiment, provided below are various attributes of the present invention.

In some embodiments, the portable ultrasound system has various attributes, including, for example, the following: (i) it is low profile; (ii) it uses a flat or concave piezoelectric material (which may be of any diameter); (iii) the piezoelectric is connected directly to the ultrasound circuit; (iv) the housing of the system is made from ultrasound transducer (and/or lens) on the front side; (v) on the back side the ultrasound generating circuit is in a low-profile housing; (vi) the transducer is driven at resonance so it has low impedance for efficient energy transfer; and (vii) the system is lightweight, efficient, and water tight.

As noted herein, the small size of the ultrasound system of the present invention can enable numerous uses and applications that have not been possible or practicable thus far. For example, the low profile ultrasound system of the present invention may be used in implantable devices and ingestible devices (e.g., smart pills). The ultrasound system of the present invention may be used for physiotherapy, drug delivery, pain management and therapy, and the like. The ultrasound system of the present invention may also be used virtually for any place one may want to apply ultrasound to at frequencies from 0-40 MHz. The internal batteries of the ultrasound system of the present invention may be supplemented with external batteries to provided extended use in various scenarios. The system may be recharged. The system may be operated by an external device. The device may also be coated with a drug or bio-compatible material to improve incorporation into the body.

Below are some aspects of the present invention that have been envisioned, including, without limitation, the following:

The Transducer. The transducer can be a 0.75-1.0 inch diameter and 2-3 MHz ultrasound generator with transducer, along with ultra efficient ultrasound generation technology built right into it. The entire transducer and electronics can be approximately the size of three quarters (or less) stacked on top of each other. The transducer can incorporate widebeam technology to spread ultrasound therapy deep into tissues and over an extensive range.

The Ultrasound Conductive Patch. The ultrasound system of the present invention can be used in tandem with an ultrasound conductive patch. Suitable patches can include, without limitation, a disposable one-time use patch for efficiently coupling ultrasound energy into tissues during activity. The patch can include ultrasound gel built into it, enabling the user to insert the transducer into the device, peel off the sticky bandage, and apply it to the appropriate location on the skin. The pain patch can be made from ultra flexible material.

The Ultrasound Power Module. The ultrasound system of the present invention can also be used in tandem with an ultrasound power module that is a light weight rectangular lithium-ion rechargeable battery pack with user interfaced pain power settings. The power module may provide low 60 mW/cm$^2$ or high 100 mW/cm$^2$ intensity of sustained therapeutic 2-3 MHz ultrasound for 6-8 hrs. The recharge time for the power module can be 1 hr after full discharge of the unit.

The Complete System. The complete system enables ultrasound therapy that is portable and in many cases unnoticeable. With the wide-beam transducer and efficient power technology the device may be used on the road, at the office, before, during, and after a sporting activity or event, and in many other situations. The ultrasound system of the present invention may also be suitable for use by amateur, grade school, collegiate, semi-professional, and professional athletes and sports teams. The ultrasound system of the present invention is suitable for use in spas, athletic training rooms, locker rooms, physical therapy offices, physicians offices, on the sidelines of sporting events, at home, and the like.

In another aspect, the present invention relates to an implantable device for use in generating ultrasound energy within a patient. The device includes the ultrasound system of the present invention and an implantable component configured to contain the ultrasound system.

In yet another aspect, the present invention relates to an ingestible device for use in generating ultrasound energy within a patient. The device includes the system of the present invention and an ingestible component configured to contain the system. A suitable ingestible component can be, without limitation, in the form of a pill In a further aspect, the present invention relates to a method for performing physiotherapy on a subject. This method involves providing the ultrasound system of the present invention and applying therapeutic ultrasound energy to a subject, where the therapeutic ultrasound energy is generated by the system of the present invention. The ultrasound energy emitted by the system is effective to penetrate deep into the tissue of the subject, and is not limited to just providing surface ultrasound energy.

In another aspect, the present invention relates to a method for applying ultrasound energy to a subject. This method involves providing the ultrasound system of the present invention and applying ultrasound energy to a surface of a subject, where the ultrasound energy is generated by the system of the present invention. The ultrasound energy emitted by the system is effective to penetrate deep into the tissue of the subject, and is not limited to just providing surface ultrasound energy. According to this method, applying the ultrasound energy to the surface of the subject can be effective to alleviate pain in tissue of the subject in and around the surface.

In a further aspect, the present invention relates to a method of topically delivering a drug to a subject. This method involves providing the ultrasound system of the present invention, where the system also includes a reservoir mounted to the piezoelectric component, the reservoir being configured to store a deliverable component in the absence of ultrasound energy generation and to release the deliverable component in the presence of ultrasound energy generation. The deliverable component comprises a drug to be delivered to a subject. According to this method, ultrasound energy is applied to a surface of a subject along with the deliverable component, where the ultrasound energy is generated by the system of the present invention. The ultrasound energy emitted by the system is effective to penetrate deep into the tissue of the subject, and is not limited to just providing surface ultrasound energy.

In another aspect, the present invention relates to a method of internally delivering a drug to a subject. This method involves administering to a subject an ingestible device of the present invention, where the ingestible component is in the form of a pill that comprises a drug to be delivered to the subject, and where the system is effective to generate ultrasound energy in order to facilitate internal delivery of the drug to the subject.

EXAMPLES

The following examples are intended to illustrate particular embodiments of the present invention, but are by no means intended to limit the scope of the present invention.

Example 1

Device Risk Assessment For Studying Pain Reduction Using Continuous Low Intensity Ultrasound Ultrasound is currently used in many medical diagnostic applications across the globe such as imaging, fetal heart rate monitoring, and blood flow analysis. Ultrasound is also present in various non-diagnostic drug delivery and therapeutic applications. The mechanical and thermal mechanisms of action in ultrasound have been shown to facilitate wound and bone fracture healing, enhance the penetration of topical ointments into the skin, provide pain and healing relief in physiotherapy, and perform non-invasive tumor and fibroid ablation.

Aggressive miniaturization and full system integration of the ultrasound transducer, electronics, and power supply has provided a unique platform solution for using ultrasound in frontline medicine. TheraSonX™ is the first truly portable Low Intensity Ultrasound (LIUS) device which can provide safe, effective relief outside of the hospital. The risk determination presented here reviews the safety research and requirements when applying ultrasound to human subjects. TheraSonX™ corresponds to one embodiment of the portable ultrasound system of the present invention that incorporates one embodiment of the low-profile ultrasound transducer of the present invention.

1. Guidelines and Regulations for Ultrasound Safety

The multitude of comingled interactions between ultrasound and biological tissues raise safety concerns stemming from undesired tissue interactions. Accordingly, the selection of appropriate parameters is crucial for the safe use of ultrasound. Several parameters including frequency, intensity, duty cycle, and application time determine the window of safe operation. Additional parameters include tissue type and environmental conditions. Associations such as the American Institute of Ultrasound in Medicine (AIUM) were created to monitor safety concerns and issue guidance to regulatory bodies such as the FDA as ultrasound continued to gain widespread acceptance in both biophysical and diagnostic fields of use. The AIUM was established in 1952 and is considered one of the most well respected sources for ultrasound safety guidance in medical applications.

The primary safety concern with ultrasound is the direct effect of ultrasonic energy on tissue. The ability of ultrasound to induce tissue effects has been quantified through two parameters: the thermal index and the mechanical index. The FDA has set upper limits on these indices for safety of diagnostic ultrasound. Extension of these limits for therapeutic applications are based on the long term studies conducted by independent research organizations and the AIUM. To date, no peer reviewed published study has shown a negative impact from properly administered ultrasound use on human subjects. This is significant given the 50 year history of ultrasound use in both diagnostic and therapeutic applications. More specifically to the TheraSonX™ range of operation, a study was conducted on low intensity ultrasound delivered over multiple days of continuous application. The study definitively showed that no adverse biological tissue effects were seen on tissue receiving 100 mW/cm² or less ultrasound intensity for over 10 consecutive days (FIG. 29) [1-3]. Given this information, the 4 hour TheraSonX™ treatments at an 80 mW/cm² intensity present a non-significant risk to subjects involved in clinical study.

2. Safety of TheraSonX™ Materials

2.1 Transducer

The majority of the materials used in the TheraSonX™ transducer are FDA approved for USP Class 6 and passed prior cytotoxicity testing. These cytotoxicity tests provide a level of safety insurance for biocompatible devices that may be implanted. Appendix 1 lists the materials with Material Safety Data Sheets (MSDS). Briefly, the transducer of TheraSonX™ is made from a lead based piezoelectric ceramic that is typical of most therapeutic ultrasound systems. To protect the clinical trial subject and the piezoelectric, the piezoelectric is completely housed in a waterproof biocompatible shell consisting of the lens, ring housing, and boot. The wire that extends from the transducer is RoHS compliant and coated in Polyvinyl Chloride (PVC). The lens and housing is made from a cross linked polystyrene. Finally, the rubber boot is made from 55A and 80A durometer polyurethanes.

2.2 Electronic Circuit, Battery and Housing

The electronic circuit uses 100% RoHS compliant components as well as printed circuit board fabrication process that are standard practice in consumer and medical electronic devices. The battery and housing also maintain RoHS certification. Appendix 1 lists general part numbers and manufactures for the electronics, battery and housing.

3. Safety of TheraSonX™ Use

The TheraSonX™ system is a medical device used to treat pain and improve quality of life for subjects. The system produces safe levels of ultrasound that have been found harmless and approved by regulatory bodies such as the FDA. Nevertheless, ultrasound is a form of energy and must be monitored and delivered appropriately to prevent possible danger to the subject. Risk is mitigated by complying with regulatory standards, maintaining good manufacturing processes, maintaining design history files, and performing failure modes and effects analysis.

3.1 Total Acoustic Power and Intensity Control

The total acoustic power and intensity from TheraSonX™ is measured during calibration procedures. Both power and intensity are directly proportional and are a function of battery voltage, transducer impedance, and frequency of operation. From a theoretical standpoint, the electrical impedance of a 25 mm diameter PZT-8 piezoelectric is approximately 12 ohms. If the piezoelectric could convert electrical energy into acoustic energy 100% efficiently, the ultrasonic power (P) in Watts would be calculated by:

$$P = \frac{V^2}{R} = \frac{\left(\frac{4}{\sqrt{2}}\right)^2}{12} = 0.67 \text{ Watts},$$

The drive voltage from TheraSonX™ is a maximum RMS value of 4/sqrt(2) volts only allowing 0.67 W of acoustic energy to possibly be generated. Since the transducer is not 100% efficient we generally measure a total acoustic power of less than 0.5 watts. The total acoustic power is spread over the entire surface area of the transducer, thereby bringing the intensity of ultrasound treatment below the safe 100 mW/cm² threshold.

3.2 Safety from Heat and Adverse Bio-effects

As ultrasonic waves move through the body, energy is absorbed in the form of heat. A traditional ultrasound therapy device operating at 1-4 W/cm² will cause harmful internal temperature increases in excess of 5° C. if left in a stationary location on the body for longer than a few minutes. This is why therapists typically apply ultrasound for short treatment times while moving the ultrasound applicator during treatment, thereby spreading the energy over an area many times the size of the transducer head. TheraSonX™ operates on the other end of the spectrum, keeping power intensities low (0.08-0.09 W/cm²) for extended treatment times in a single location while using a custom convex transducer designed to spread the energy over a large area underneath the skin layer. Ultrasonic temperature analysis shows that continuous ultrasound application below 0.5 W/cm² results in safe temperature increases of 1-4° C. [1-3]. A subject could wear this device for many days with no thermal bio-safety concerns. This study suggests an intensity safety threshold even higher than the 0.1 W/cm² guidance from the American Institute of Ultrasound in Medicine (AIUM).

TheraSonX™ operates within established FDA parameters for safe use over a continuous timeframe. The following chart was taken from the "Guidance for Industry and FDA Staff," FDA, September 2009:

TABLE 2-1

Pre-amendments Acoustic Output Exposure Levels (mW/cm²)

| Use | $I_{SPTA}$ | $I_{SPPA}$ or MI |
|---|---|---|
| Peripheral Vessel | 720 | 190 or 1.9 |
| Cardiac | 430 | 190 or 1.9 |
| Fetal Imaging | 94 | 190 or 0.28 |
| Ophthalmic | 17 | 28 or 0.23 |

Figure 29:
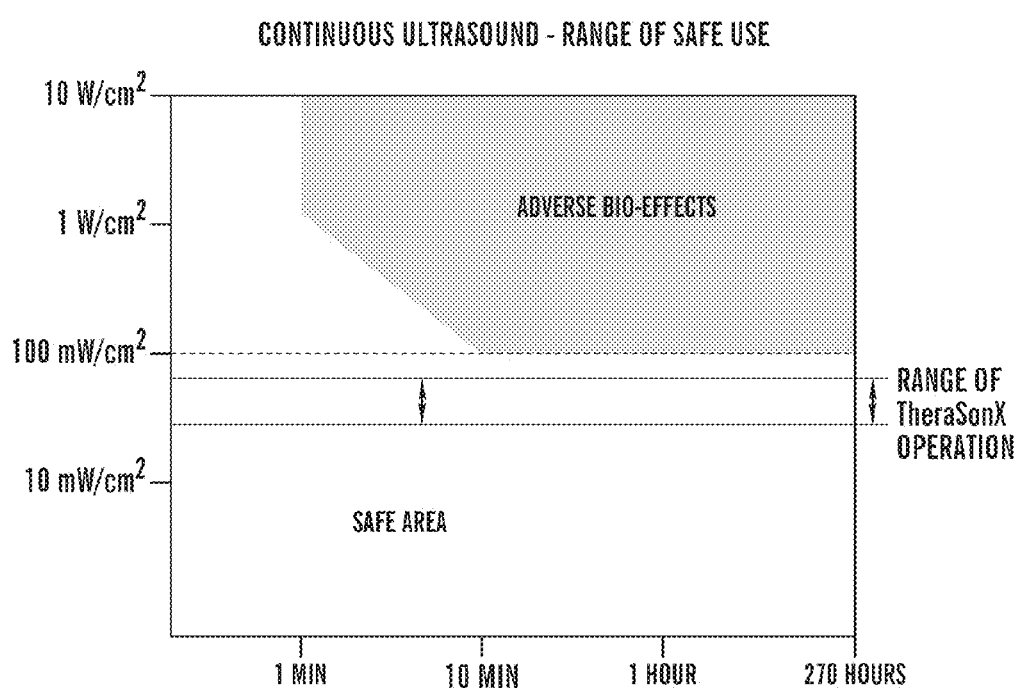
FIG. 29 is a graph of guidelines from the American Institute of Ultrasound in Medicine. As shown, no adverse bio-effects are found with 100 mW/cm$^2$ ultrasound application over extended treatment periods.

$I_{STPA}$ = Derated Spatial-Peak Temporal-Average Intensity
$I_{SSPA}$ = Derated Spatial-Peak Pulse-Average Intensity
MI = Mechanical Index The guidance above is based in large part on the research and guidelines published by the American Institute of Ultrasound in Medicine (AIUM). A recent study published by the AIUM journal offers additional guidelines for emerging research and clinical applications of LIUS on humans. FIG. 29 summarizes the AIUM guidelines [1-3]:

Power output from the TheraSonX™ device is preset at a low intensity (80-90 mW/cm²) and cannot be modified by the user.

3.3 Safety of TheraSonX™ Compared to FDA Approved Predicate Devices

Another measure of safety is to compare the TheraSonX™ device to already FDA approved ultrasound devices on the market today. The following device has already been approved by the FDA for extended Low Intensity Ultrasound (LIUS) treatments: NanoVibronix "Painshield"—FDA 510(k) (K081075) approved in June, 2008 to apply ultrasonic energy to generate heat within body tissues for the treatment of selected medical conditions such as relief of pain, muscle spasms, and joint contractures. More data for predicate devices can be found in the Regulatory Path Details section of this compilation.

3.4 Safety Settings of TheraSonX™ and MI & TI Calculations

As discussed in the background section, MI is a standard measure of the acoustic output in ultrasound systems defined as the peak rarefactional pressure of an ultrasound longitudinal wave propagating in a uniform medium, divided by the square root of the center frequency of the transmitted ultrasound wave. According to the FDA for diagnostic obstetrics application, the MI should not exceed 1.9. In order to calculate the MI achieved in TheraSonX™ using S.I. units (f=2.7 MHz, I=900 W/m²), we will use the intensity (I) and acoustic impedance of muscle tissue (Z=1.6e6 kg/m²s) in order to calculate the pressure (P) and derived the following formula for TheraSonX™ to calculate a MI of 0.023 according to:

$$MI = \frac{P}{\sqrt{f}} = \frac{\sqrt{I \cdot Z}}{\sqrt{f}} = \frac{\sqrt{900 \cdot 1.5e6}}{\sqrt{2.7}} \times 10^{-6} = 0.023$$

Another standard measure is the thermal Index (TI). TI is defined as the ratio of the emitted acoustic power to the power required to raise the temperature of tissue by 1° C. The TI is intended to indicate the likely temperature rise that might be produced after long exposure. A larger TI value represents a higher risk of damage due to temperature increases. For therapeutic applications the FDA requires that TI's over 6 require further explanation and safety analysis [4]. The calculated soft-tissue thermal index ($T_s$) for the ultrasound intensity (I) and transducer area (A) for TheraSonX™ is 5.6 as calculated by:

$$T_s = \frac{I \cdot A \cdot f}{210} = \frac{(0.09)(4.91)(2.7e3)}{210} = 5.6$$

The calculated MI is less than 1.9 and the $T_s$ value achieved is less than 6 for TheraSonX™. The system is therefore safe according to established FDA guidelines. It should also be noted that the calculated MI and TI for TheraSonX™ slowly decrease as the system losses battery charge and that it is physically impossible (due to battery voltage and electrical restrictions) for the system to produce levels of ultrasound that would cause mechanical or thermal damage to the tissue.

3.5 Additional Safety Considerations for Implants and Use

Adverse effects on artificial implants due to the mechanical ultrasound waves—Detailed research on the effects of low intensity ultrasound on artificial implants has not yet been performed, therefore initial trials will exclude the use of TheraSonX™ on people with artificial implants.

Misplacement of the device—Exact placement of the device around the treatment area is not critically important because ultrasound waves reflect and refract inside the body, thereby treating a much larger area then the transducer diameter.

Improper placement of the device directly over a bone may significantly reduce the effectiveness of the device. If the transducer is placed in such a manner that it does not make solid contact with the skin (for instance placed over a small bone which resides directly under the skin's surface eg. tip of an elbow), then ultrasound waves may not be efficiently transferred through the skin.

Leaving the device on for extended periods of time—Ultrasound at TheraSonX™ intensity (80-90 mW/cm$^2$) can be emitted into the body continuously for over 10 days without causing any adverse bio effects to the tissue [1-3]. If the subject is unconscious or for some reason was not able to remove the device for a long period of time, TheraSonX™ would not be a safety issue because A) it will run out of battery power (maximum 6 hrs) and stop emitting ultrasound altogether, B) if the device was plugged into the recharger during use, it would be safe for 10 consecutive days, C) the bandages used to hold the transducer in place are biocompatible for extensive use periods (greater than 48 consecutive hours).

Use during recharging—TheraSonX™ is able to be used while it is recharging. The battery box will become warm during recharging, but remains within safe thermal limits due to intelligent charging built into TheraSonX™. Internal circuitry monitors the recharging process and any change in voltage, current, or thermal temperature outside of specified limits will result in a shutdown. Additionally, since the battery box is not attached to the body directly, it does not represent a threat to the subject.

Submerging the device in water (or other liquid)—Submersion into liquid does not affect the transducer at all. It is submerged in water during the FDA dictated testing procedures conducted in our laboratories and is therefore completely waterproof and electrically isolated by design.

The battery box is water resistant and may be used in humid and damp environments but is not water proof (similar to a cell phone). If the battery box is submerged in water by accident, the electronics and battery may become damaged, however there is minimal risk for painful or life threatening shock since the device operates at less than 4 Volt power level. We mitigate the risk to subjects for potential shock by encasing electrodes, wires, circuits and all of the electronic components in additional non-conductive material, before it is enclosed in the battery box housing.

In the event the battery box is submerged in water during recharge, there is no additional risk for electrical shock. The charger supplies a 4.2 Volt isolated recharge power with internal short circuit detection to prevent electrical shock.

Device stops working mid treatment—The body does not require this device to be active in order to function properly. There is no safety issue if the device stops operating mid treatment.

Change in Gait—Placement of the non-invasive device is accomplished using a flexible patch that does not restrict the subject's movement or cause additional risk to the subject. The wire between the battery and transducer does not wrap around or otherwise hinder the movement during normal use. The wire is kept short to prevent risk of tripping or "snagging" on objects during movement. When wearing clothing the transducer and wiring will be concealed beneath the clothing and the battery housing will be secured by belt clip case or in the pocket, further reducing risk of snagging or tripping.

Use in Children—Children will be excluded from clinical trials.

Use by Pregnant Women—Pregnant women will be excluded from clinical trials.

3.6 Subject Self Assessment

Subjects involved in the clinical trial will receive an orientation and directions for appropriate use prior to receiving a device for treatment. Subjects will be instructed to:

Remove the device if any painful heating is felt

Investigate area where the applicator will be attached prior to treatment each day. We expect the area under the transducer to be red immediately following treatment due to increased blood flow. However, if the redness remains overnight and is still present immediately prior to the next treatment, subjects will be instructed to discontinue treatment 4. Output Measurements Various measurements and calibration protocols are utilized to test devices for acoustic power output, intensity, resonance frequency, and system battery life. Additionally, a general quality insurance inspection is performed to make sure all wires, circuit components, and housing are secured and safe for use.

Figure 30A:
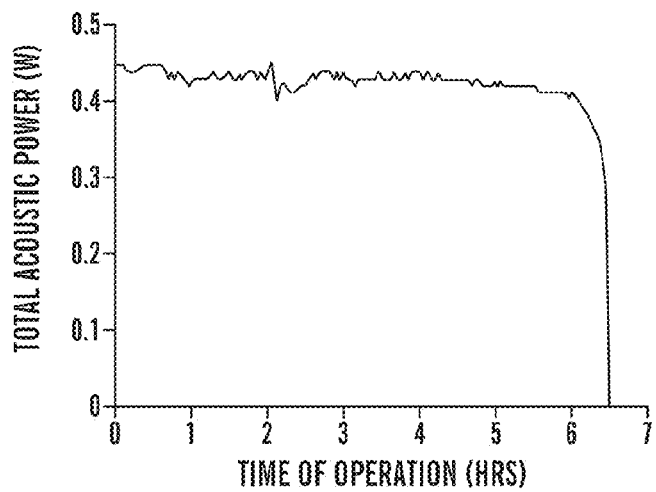
FIGS. 30A-30C are graphs showing system measurements of one embodiment of the portable ultrasound system (TheraSonX™) of the present invention.
Figure 30B:
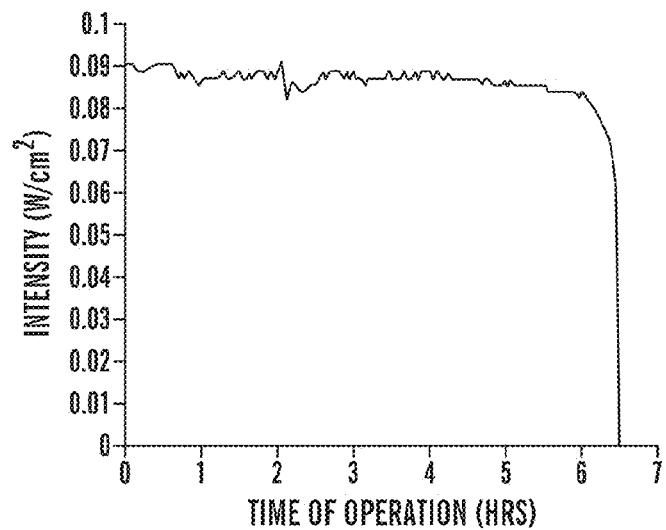
Figure 30C:
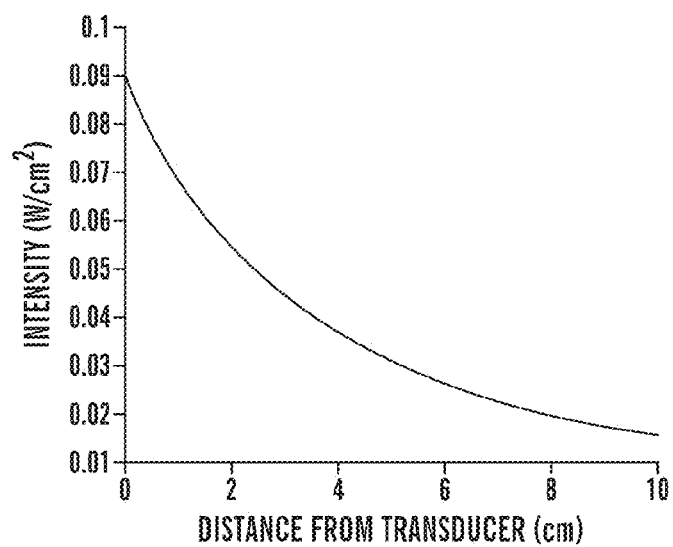

Acoustic power and intensity measurements—Acoustic power is measured using a calibrated acoustic power meter from Ohmic Instruments (www.ohmicinstruments.com) with 2 mW ultrasound power resolution. The TheraSonX™ transducer is placed in a power meter filled with degassed water, the meter is zeroed, and the TheraSonX™ unit is turned on. The ultrasound energy radiated from transducer causes a force that is detected on a power meter calibrated in acoustic watts (W). The power meter is connected to a computer via USB to log measurement data from TheraSonX™ every 2 minutes until the battery of the device is completely diminished and the system turns off. The TheraSonX™ system produces a total acoustic output power of 440-460 mW at full system charge and slowly decreases over the charge cycle of the device to a steady state 380-400 mW of acoustic power (shown in FIG. 30A from TheraSonX™ units measured in lab). The spatial average acoustic intensity is calculated by a mathematical calculation: dividing the total acoustic power, by the surface area of the transducer. In example: the TheraSonX™ transducer is 25 mm in diameter, so the acoustic intensity from the device at full charge is $0.45\ W/(\pi*1.25^2\ cm) = 92\ mW/cm^2$. The output intensity of TheraSonX™ is shown in FIG. 30B for over 6 hrs. Finally, the 10° diverging lens on the device increases the treatment area in addition to natural divergence of the acoustic beam according to: $r=1.25+\tan(10°)*x$; where r is the radius of the circular area being treated in cm and x is the distance from the face of the transducer in cm. The ultrasound intensity as it relates to distance from the transducer is calculated by: $I=Power/(\pi*(1.25+\tan(10°)*x)^2)$ where I is the intensity of the acoustic beam in $W/cm^2$ as shown in FIG. 30C.

Figures 31A, 31B:
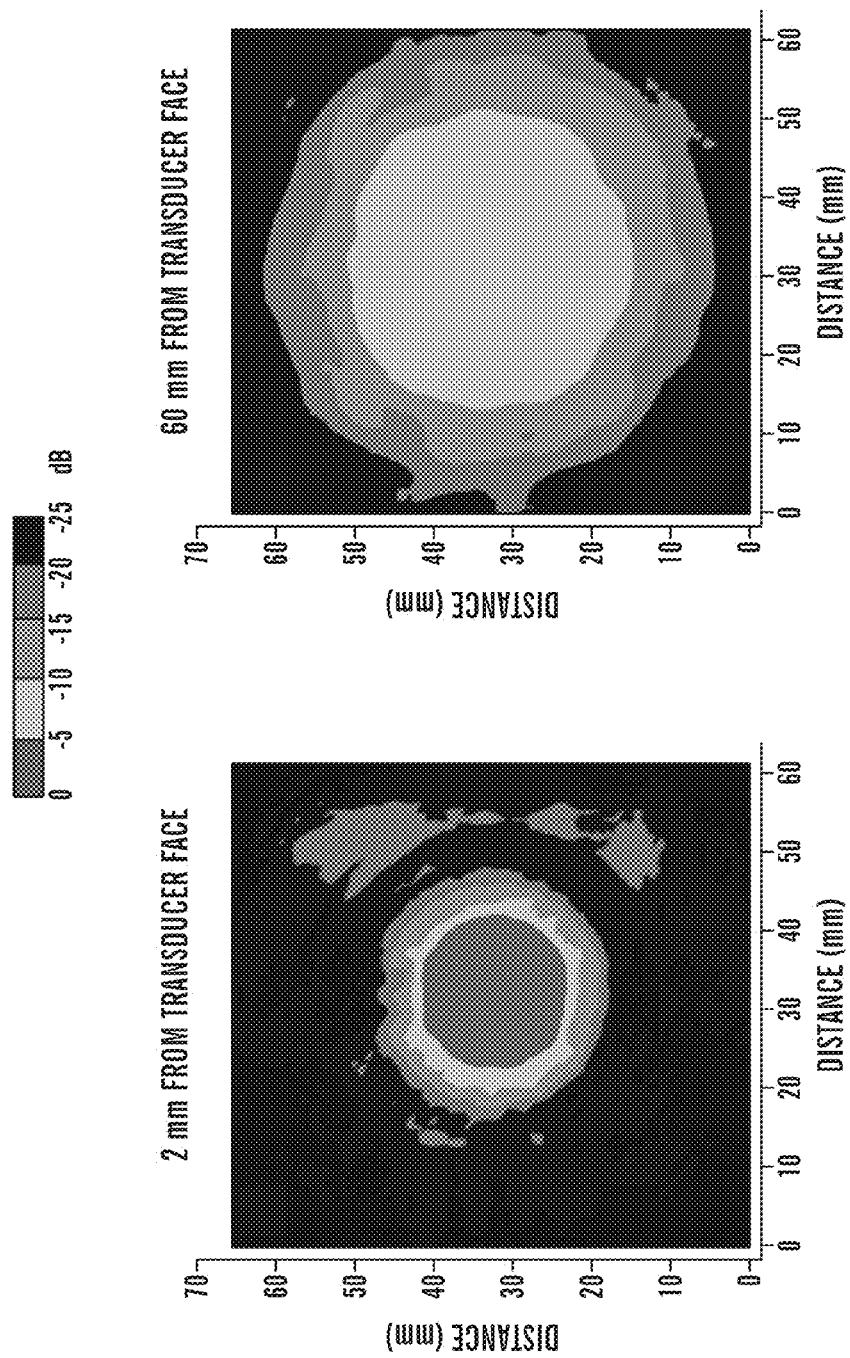
FIG. 31 shows beam measurements of one embodiment of the portable ultrasound system (TheraSonX™) of the present invention. A: 2 mm from transducer. B: 60 mm from transducer.

Peak spatial and temporal ultrasound intensity is measure using a beam scanning system in conjunction with a calibrated hydrophone (www.onda.com). The beam scanning system is also used to characterize the width of the ultrasound acoustic field during development of the transducer lenses. FIG. 31A shows the measured acoustic intensity field from the TheraSonX™ transducer with 10° lens 2 mm (A) and 60 mm (B) from the face of the transducer.

5. Safety Assessment Conclusion

Under 21 CFR 812.3(m), a Significant Risk (SR) device is an investigational device that:

Is intended as an implant and presents a potential for serious risk to the health, safety, or welfare of a subject;

Is purported or represented to be for use supporting or sustaining human life and presents a potential for serious risk to the health, safety, or welfare of a subject;

Is for a use of substantial importance in diagnosing, curing, mitigating, or treating disease, or otherwise preventing impairment of human health and presents a potential for serious risk to the health, safety, or welfare of a subject; or Otherwise presents a potential for serious risk to the health, safety, or welfare of a subject.

Conversely, a Non-Significant Risk (NSR) device is one that does not meet the definition for an SR device (above).

The system under evaluation is completely non-invasive and will never be implanted during the course of treatment. The system is not used to sustain life and is not a critical element in diagnosing or treating any life threatening condition. According to guidance released by the FDA (table 2-1) and studies performed by the American Institute of Ultrasound in Medicine (FIG. 1), the system under evaluation does not present a potential for serious risk to the health, safety, or welfare of the subject.

6. FDA Guidance for TheraSonX Evaluation

The FDA was contacted via phone to provide guidance related to the safe evaluation of TheraSonX™ in clinical testing prior to FDA approval. Phone conversations with the FDA Office of Device Exemption validated the NSR intensity levels referenced in Table 2-1. These are threshold levels of intensity that determine whether a change (by the manufacturer) in a diagnostic Ultrasound device's output warrants a new FDA safety review. If the change in intensity is below the thresholds in Table 2-1, NO amendment is necessary because the change in observed in bio-effects is zero or near zero.

This feedback from the FDA compliments our determination that the device is a non-significant risk. As a NSR device, no formal review by the FDA is required prior to IRB approved clinical testing.

REFERENCES

[1] AIUM. Bioeffects considerations for the safety of diagnostic ultrasound. J Ultrasound Med. 7(Suppl):S1-S38. (1988).
[2] AIUM. Bioeffects and safety of diagnostic ultrasound. Laurel, M D: American Institute of Ultrasound in Medicine; (1993).
[3] AIUM. Mechanical bioeffects from diagnostic ultrasound: AIUM consusus statements. J Ultrasound Med. 2000; 19:67-170. (2000).
[4] U.S. FDA Section 510(k) guidance to manufacturers on therapeutic ultrasound devices for submissions and clearance. February (1993).
[5] Diathermy, ultrasonic, for use in applying therapeutic deep heat, U.S. FDA 510(k) ultrasound therapy device approval K081075. (2008)
[6] Suslick K S, Ultrasound: Its Chemical, Physical, and Biological Effects. VCH Publishers, New York. (1988).
[7] Kinsler L E, Frey A R, Coppens A B, Sanders J S, Fundemaentals of Acoustics. John Wiley and Sons, New York. (1980).
[8] Ensminger D, Ultrasonics: Fundamentals, Technology, Applications. Marcel Dekker, New York. (1988).
[9] Mast D, Empirical relationships between acoustic parameters in human soft tissues. Acoust. Res. Lett. 1, 37-42 (2000).
[10] Suslick K S, Nyborg W L, Ultrasound: its chemical, physical, and biological effects. J. Acoust. Soc. Am. 87, 919-920. (1990).
[11] Barnett S B, Rott H D, ter Haar G R, et al. The sensitivity of biological tissue to ultrasound Ultras. Med. Bio. 23, Issue 6, 805-812. (1997).
[12] Linder J R, Song J, Christiansen J, et al. Ultrasound Assessment of Inflammation and Renal Tissue Injury With Microbubbles Targeted to P-Selectin. Circulation, 104, 2107-2112. (2001).
[13] Wong R A, Schumann B, Townsend R, Phelps C A. A Survey of Therapeutic Ultrasound Use by Physical Therapists Who Are Orthopaedic Certified Specialists. PHYS THER Vol. 87, No. 8, pp. 986-994. (2007).
[14] Warden S J, McMeeken J M. Ultrasound usage and dosage in sports physiotherapy. Ultrasound Med Biol; 28: 1075-1080. (2002).
[15] Currier D P, Kramer J F. Sensory nerve eonduetion: heating effects of ultrasound and infrared. Physiotherapy Canada, 34 (5): 241-246. (1982).
[16] Noble J G, Lee V, Griffith-Noble F. Therapeutic ultrasound: The effects upon cutaneous blood flow in humans. Ultrasound in Medicine & Biology, Volume 33, Issue 2, Pages 279-285
[17] Feril Fr. L B, Tachibana K, Ogawa K, et al. Therapeutic potential of low-intensity ultrasound (part 1): thermal and sonomechanical effects. 1346-4523 (Print) 1613-2254 (Online) Issue, Volume 35, Number 4. (2008).
[18] Hogan R D, Franklin T D, Fry F J, Avery K A, Burke K M. The effect of ultrasound on microvascular hemodynamics in skeletal muscle: effect on arterioles. Ultrasound in Medicine & Biology, Volume 8, Issue 1, Pages 45-47, 49-55 (1982).
[19] Nyborg W L. Biological effects of ultrasound: development of safety guidelines: Part I: personal histories Ultrasound in Medicine & Biology, Volume 26, Issue 6, Pages 911-964 (2000).
[20] U.S. FDA Section 510(k) guidance to manufacturers on therapeutic ultrasound devices for submissions and clearance. February (1993).
[21] Singh V R. Safety Standard for Medical Ultrasound Systems. IEEE standards of Proc. IFMBE 4-15 (2007).
[22] Adler R. Future And New Developments In Musculoskeletal Ultrasound. Radiologic Clinics of North America, Volume 37, Issue 4, Pages 623-631
[23] Peat G, McCarney R, Croft P. Knee pain and osteoarthritis in older adults: a review of community burden and current use of primary health care. Ann Rheum Dis.; 60: 91-98 (2001).

APPENDIX 1

Transducer and Circuit Material MSDS and Safety Information

Transducer Material:
1. Transducer Housing and Lens:
   Material Name Rexolite®
   Material: Cross-linked Polystyrene
   Manufacturer: C-Lec Plastics Inc.
   MSDS: www.sdplastics.com/pdf/REXOLITE1422MSDS.pdf
   General Information about Rexolite®: www.ejbplastics.com/pdf/datasheets-plastics/Rexolite.pdf 2. Transducer Rubber Boot:
   Material Name: STERalloy FDG 2056, 2781
   Material: Polyurethane
   Manufacturer: Hapco Inc.
   MSDS: www.hapcoweb.com/_private/BROCHURES/PDF_Format/Steralloy.pdf
   General info: www.ides.com/pweb/obds.aspx?E=126426
3. Piezoelectric Crystal:
   Material Name: PZT-8
   Material: Lead Zirconate Titanate
   Manufacturer: Steiner & Martins Inc.
   MSDS: www.seas.upenn.edu/~nanofab/chemicals/MSDS_PZT.pdf
   General info: www.docstoc.com/docs/5304960/Approved-By-MORGAN-ELECTRO-CERAMICS-Document-m-MS-Approved/
4. Transducer Wire:
   Material Name: Coaxial Cable
   Material: NMEF1/22 1 5044SJ
   Manufacturer: Cooner Wire Inc.
   Wire satisfies RoHS compliance.

Electronics and Housing:
1. Housing of System:
   Material Name: Minitec Enclosure
   Material: ABS (UL 94 HB)
   Manufacturer: OKW Enclosures Inc.
   MSDS: www.plasticsmadesimple.com/DataSheets/ABS_MSDS_GP.pdf
   General info: www.okwenclosures.com/products/okw/minitec.htm
2. Printed Circuit Board:
   Material Name: Printed Circuit Board
   Material: Multiple
   Manufacturer: Sunstone Circuits Inc.
   RoHS: www.sunstone.com/pcb-capabilities/lead-free-rohs/material-comparison.aspx
   General info: www.sunstone.com
3. Electronic Circuit Components:
   We use a variety of manufactures which include: Fairchild Semiconductor Inc., International Rectifier Inc., On-semi Conductor Inc., Panasonics Inc., Intersil Inc., Dialight Inc. and Texas Instruments Inc.
   All components satisfy RoHS compliance.
4. Battery Pack:
   Material Name: Polymer Lithium Ion 3.7V Cell
   Material: Multiple
   Manufacturer: EMAX Inc.
   Info: rfi.com.cn/en/EMAX %200EM %20Catalogue0910.pdf
   Data Sheet: www.batteryspace.com/prod-specs/4312.pdf Example 2

UltrOZ Therapeutic Case Study

Splint Reduction

History: Subject was a 2 yr old thoroughbred filly. The filly had been in race training on a farm and was moving up to the next level of training by coming to the Churchill Downs race track.

Evaluation: The filly arrived at the track with a large splint on the right front leg, medial aspect. The filly was not lame on arrival or through the days of UltrOZ ultrasound treatment.

Treatment: The UltrOZ unit was applied to the caudal aspect of the splint, covering the suspensory ligament as well. It was applied from 10 a.m. to 3 p.m. every day, 7 days a week from October 22 to November 20. No other treatments were performed.

Outcome: The filly never exhibited any soreness in the suspensory ligament, which is unusual with splints this size. The splint was reduced in size by 30% over the 4 week period of use. The trainer and Equine Therapist were very happy with the results of treatment. The reduction of splint size during an increase in exercise activity was atypical and positively correlated with the use of the UltrOZ therapeutic unit.

Example 3

Horse Case Study

Horse Subject: 9 year old, thoroughbred, gelding. Mid level event horse.

History: Acute presentation of 3/5 lameness on the right forelimb.

Assessment: A new splint had formed on the proximal aspect of the 4th metacarpal bone of the right fore. The horse blocked to regional local anesthesia of the splint and suspensory ligament. Radiographs revealed no fracture but active periosteal proliferation of the splint. Ultrasound of the suspensory ligament showed mild inflammation at the region associated with the splint.

Treatment: The horse was treated with the anti-inflammatory Equioxx for 10 days. A regional injection at the splint/suspensory interface of betamethasone/serapin/predef was done. The horse was stall rested for 7 days, stalled and tack walked for 7 days. Small paddock with tack walk for remainder of 30 days.

A prototype Zetroz therapeutic ultrasound unit was utilized beginning 2 days after the initial injection for 3 weeks. The unit was used under a standing bandage to hold in place. The unit stayed in place for overnight treatment every day for 3 weeks with no difficulties.

Outcome: The horse was 40% improved at 7 days, 100% sound at 2 weeks. The splint reduced in size 50% by week 3. The speed of return to soundness and the rapid reduction in the size of the splint were the atypical components of the outcome compared to the normal case. The horse has remained sound back into work 6 weeks later.

Example 4

UltrOZ™ Therapeutic Ultrasound Case Study

General Injury Prevention &

Reduction for Polo Horses

This study covered five horses in 12 weeks:

1. Arthritic Symptoms & Lameness: The first horse is a mare who had arthritic symptoms in her right front knee, especially prevalent when being shod. To alleviate stiffness we used the UltrOZ™ ultrasonic device. She continued to work and we found less reaction in the knee during her next round of shoeing.

2. Bruise Reduction: The second horse is a mare who incurred a sole bruise in her right front foot before we could get her shod after summer rest on September 28th. Once the bruise was discovered we got her shod and applied the ultrasound treatment. Sole bruises can take two months to heal. This horse was sound in three weeks after the initiation of daily UltrOZ™ treatments and has been back to full work with no further issue.

3. Contusion Inflammation Reduction: The third horse is a mare who received a contusion on the outside of her right front leg over the suspensory area about half way up the cannon bone. The contusion caused inflammation with a slight skin abrasion over the outside of the leg. Wrapping cold hosing and UltrOZ™ ultrasound treatments were applied. The horse was tender on the spot and was given two days of rest. After only two weeks of treatments the swelling disappeared as she continued to work. This rate of healing was quicker than expected based on observations of previous recovery times for similar cases. This horse subject has experienced no further problems.

4. Open Wound/Laceration Reduction: The fourth horse is a gelding who incurred a 1½ inch laceration ⅔ of the way up the cannon bone on the outside of the right front. The injury was only through the first layer of skin and was not deep. Due to the partial location of the wound over the suspensory ligament we did not want to suture. Along with cleaning, wrapping, and topical ointment we applied the UltrOZ™ ultrasound treatment. He was never lame but the injury was given 1 week to heal before returning to normal work. The swelling is slight but controlled and the wound has healed over quite well with very minimal scar tissue. It is believed that the UltrOZ™ treatment assisted in speeding the recovery time as compared to previously observed wounds of this type.

5. Superficial Tendon Strain: The fifth horse is a mare who received a strain to the superficial tendon in her left front leg. The injury occurred on November 19th and the UltrOZ™ ultrasound treatment was applied in addition to cold hosing. By December 5th (two weeks later) the horse was completely sound and the inflammation and swelling were gone by week three. The rate of return to soundness in this case was quicker than experienced in the past with this type of injury.

Conclusion: In each of these cases we used the equipment provided along with vet wrap to hold the unit and disk in place. The conditions on which the equipment has been used has shown increased speed of the healing and return to soundness from what is traditionally seen.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. A low-profile ultrasound transducer comprising:
  a piezoelectric component operative to receive a driving signal from an energy generating module and to emit the driving signal as ultrasonic energy, said piezoelectric component having a front surface and a back surface, and said energy generating module comprising a plurality of electronic components comprising a power source, an oscillator, and a driver component; and
  a lens component directly or indirectly deposited on the front surface of the piezoelectric component, said lens component comprising a lens portion and a support portion,
  wherein the lens portion of the lens component is configured to control the direction and wave pattern of the ultrasonic energy emitted from the piezoelectric component, and
  wherein the support portion of the lens component is configured to hold the piezoelectric component in place and to provide a chamber for housing at least one electronic component of the energy generating module.

2. The low-profile ultrasound transducer according to claim 1, wherein the plurality of electronic components of the energy generating module further comprises an electronic component selected from the group consisting of a temperature sensor and a wireless recharger component.

3. The low-profile ultrasound transducer according to claim 1, wherein the piezoelectric component is effective to transmit ultrasonic energy having an acoustic intensity ranging from between about 10 mW/cm$^2$ and about 5 mW/cm$^2$.

4. The low-profile ultrasound transducer according to claim 1, wherein the lens portion is configured to emit ultrasonic energy in a wave pattern selected from the group consisting of a diverging wave pattern, a scattering wave pattern, a focused wave pattern, a parallel wave pattern, and a directed waveform at any angle from 1 to 180 degrees from a surface.

5. The low-profile ultrasound transducer according to claim 1, wherein the lens portion comprises a convex lens or a ridged lens, said convex lens configured to emit the ultrasonic energy in a diverging wave pattern and said ridged lens configured to emit the ultrasonic energy in a scattering wave pattern.

6. The low-profile ultrasound transducer according to claim 1, wherein said lens component spreads ultrasonic energy emitted from the piezoelectric component for ultrasound therapy from an angle ranging from between about 0 degrees and about 180 degrees.

7. The low-profile ultrasound transducer according to claim 1, wherein the support portion is configured as a ring having an outer ring portion and an inner ring portion, said inner ring forming a ring-like shelf within the outer ring effective to hold the piezoelectric component in place.

8. The low-profile ultrasound transducer according to claim 1, wherein the lens portion and the support portion form a single lens component, said lens portion forming a front end base portion of the chamber, and said support portion forming a support wall of the chamber, said support wall extending in a backward direction from the front end base portion.

9. The low-profile ultrasound transducer according to claim 8, wherein the support wall contains a wireless recharger coil.

10. The low-profile ultrasound transducer according to claim 8 further comprising:
  a cover deposited over the support wall to substantially close the chamber.

11. The low-profile ultrasound transducer according to claim 8, wherein the at least one electronic component of the energy generating module housed in the chamber includes one or more electronic component selected from the group consisting of a power source, an oscillator, a driver component, a temperature sensor, and a wireless recharger component.

12. The low-profile ultrasound transducer according to claim 8, wherein the at least one electronic component is separated from the piezoelectric component by a layer of air.

13. The low-profile ultrasound transducer according to claim 8, wherein the at least one electronic component is a temperature sensor either mounted onto the piezoelectric component or deposited near but not onto the piezoelectric component.

14. The low-profile ultrasound transducer according to claim 1, wherein said piezoelectric component is air backed or vacuum backed to increase ultrasonic energy propagation in a forward direction.

15. The low-profile ultrasound transducer according to claim 1, wherein said lens component allows light energy to pass through it, said light energy being emitted through the lens component through the front surface of the piezoelectric component.

16. The low-profile ultrasound transducer according to claim 1 further comprising:
a light source or a plurality of light sources securely deposited in proximity to the piezoelectric component and/or the lens component.

17. The low-profile ultrasound transducer according to claim 16, wherein the light source is a light-emitting diode (LED), a laser, or a combination thereof.

18. The low-profile ultrasound transducer according to claim 16, wherein the light source is set inside of the lens component, inside the piezoelectric component, or inside both the lens component and the piezoelectric component.

19. The low-profile ultrasound transducer according to claim 16, wherein light source is set substantially in the center of the lens component, the piezoelectric component, or both the lens and piezoelectric components.

20. The low-profile ultrasound transducer according to claim 16, wherein the light source is wired to a front conductor of the piezoelectric component and a back conductor of the piezoelectric component, thereby allowing the driving signal to the piezoelectric component to power the light source.

21. The low-profile ultrasound transducer according to claim 16, wherein the light source is wired around the piezoelectric component or through the piezoelectric component.

22. The low-profile ultrasound transducer according to claim 16, wherein the light source is configured to be powered either in series or in parallel with the piezoelectric component.

23. The low-profile ultrasound transducer according to claim 1, wherein the piezoelectric component is integrated into a portable ultrasound system.

24. The low-profile ultrasound transducer according to claim 23, wherein the portable ultrasound system comprises:
an energy generating module comprising a power source, an oscillator, and a driver component coupled to the low-profile ultrasound transducer.

25. A multi-unit transducer comprising:
a plurality of ultrasound transducers combined into a single multi-unit transducer,
wherein at least one of the plurality of ultrasound transducers is a low-profile ultrasound transducer according to claim 1.

26. The multi-unit transducer according to claim 25, wherein the plurality of ultrasound transducers comprise transducers of either the same or different functions and/or sizes.

27. A low-profile ultrasound transducer comprising:
a piezoelectric component operative to receive a driving signal from an energy generating module and to emit the driving signal as ultrasonic energy, said piezoelectric component having a front surface and a back surface, and said energy generating module comprising a power source, an oscillator, and a driver component; and
a lens component directly or indirectly deposited on the front surface of the piezoelectric component, said lens component comprising a lens portion and a support portion,
wherein the lens portion of the lens component is configured to control the direction and wave pattern of the ultrasonic energy emitted from the piezoelectric component, and
wherein the support portion of the lens component is configured to hold the piezoelectric component in place and to provide a chamber for housing the oscillator and driver component of the energy generating module.

28. A low-profile ultrasound transducer comprising:
a piezoelectric component operative to receive a driving signal from an energy generating module and to emit the driving signal as ultrasonic energy, said piezoelectric component having a front surface and a back surface, and said energy generating module comprising a power source, an oscillator, and a driver component; and
a lens component directly or indirectly deposited on the front surface of the piezoelectric component, said lens component comprising a lens portion and a support portion,
wherein the lens portion of the lens component is configured to control the direction and wave pattern of the ultrasonic energy emitted from the piezoelectric component, and
wherein the support portion of the lens component is configured to hold the piezoelectric component in place and to provide a chamber for housing the power source, oscillator, and driver component of the energy generating module.

* * * * *